US010849703B2

(12) United States Patent
Backhaus et al.

(10) Patent No.: US 10,849,703 B2
(45) Date of Patent: Dec. 1, 2020

(54) GLOVE DISPENSING CARTRIDGE, DISPENSING APPARATUS AND METHOD FOR USE THEREOF

(71) Applicant: Glovematic Pty Limited, Hornsby (AU)

(72) Inventors: Stephan Backhaus, Hornsby (AU); Michelle Rosevear, Hornsby (AU); Ryan Mischkulnig, Hornsby (AU); Mark Bayly, Hornsby (AU)

( * ) Notice: Subject to any disclaimer, the term of this patent is extended or adjusted under 35 U.S.C. 154(b) by 0 days.

(21) Appl. No.: 16/206,335

(22) Filed: Nov. 30, 2018

(65) Prior Publication Data

US 2019/0167371 A1   Jun. 6, 2019

Related U.S. Application Data

(63) Continuation of application No. PCT/AU2017/050528, filed on Jun. 1, 2017.

(51) Int. Cl.
| B65D 83/08 | (2006.01) |
| A61B 42/50 | (2016.01) |
| A61B 42/40 | (2016.01) |
| B65H 3/08 | (2006.01) |
| A47G 25/90 | (2006.01) |
| A61B 50/20 | (2016.01) |

(52) U.S. Cl.
CPC ............ *A61B 42/40* (2016.02); *A47G 25/904* (2013.01); *A61B 42/50* (2016.02); *A61B 50/20* (2016.02); *B65D 83/08* (2013.01); *B65H 3/08* (2013.01); *B65H 3/0816* (2013.01); *B65D 83/0835* (2013.01)

(58) Field of Classification Search
None
See application file for complete search history.

(56) References Cited

U.S. PATENT DOCUMENTS

| 1,462,906 | A | 7/1923 | Graeff |
| 6,932,253 | B2 | 8/2005 | Sato |
| 7,712,642 | B2 * | 5/2010 | Gaines ................ A47G 25/904 223/111 |
| 2011/0283439 | A1 | 11/2011 | Backhaus et al. |

FOREIGN PATENT DOCUMENTS

| GB | 2516649 A | 2/2015 |
| WO | 2005013842 A2 | 2/2005 |
| WO | 2014063392 A1 | 5/2014 |

\* cited by examiner

*Primary Examiner* — Gene O Crawford
*Assistant Examiner* — Ayodeji T Ojofeitimi
(74) *Attorney, Agent, or Firm* — Morriss O'Bryant Compagni Cannon PLLC

(57) ABSTRACT

A cartridge for receiving a plurality of adjacent, aligned, disposable gloves is described, the cartridge comprising a base; and a first element being arranged in use for alignment of the finger portions of the plurality of gloves. Furthermore, a machine arranged for dispensing a disposable glove is described, the machine comprising: an articulated arm arranged in use for contacting and retaining a first part of the glove and for moving said glove from a first position in which the glove is located in a cartridge containing one or more gloves, to a second position in which a second part of the said glove is able to be contacted with and retained by an anchoring means to open the cuff to allow a user to don the glove.

19 Claims, 27 Drawing Sheets

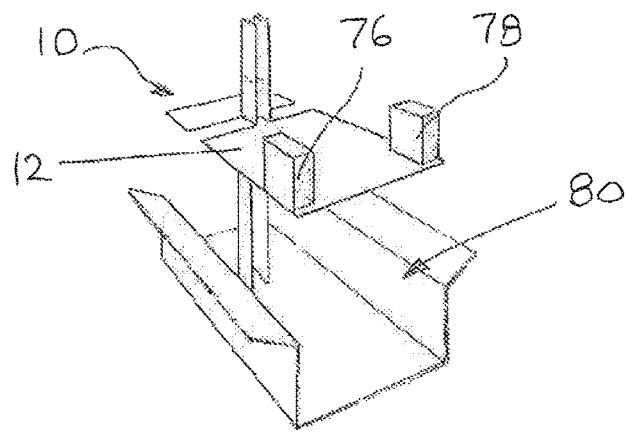
FIG. 15(a)
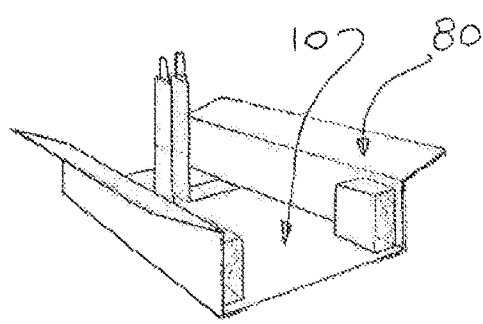
FIG. 15(b)
FIG. 16(a)
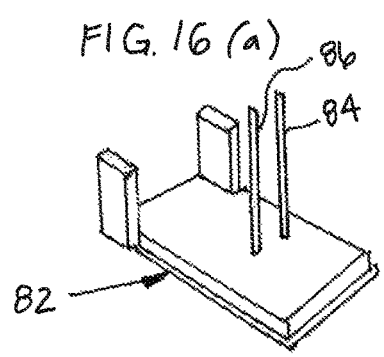
FIG 16(b)
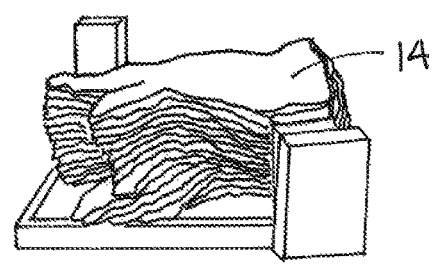
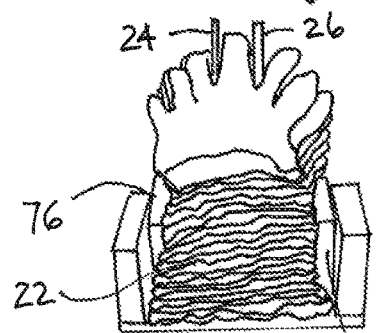
FIG. 16(c)
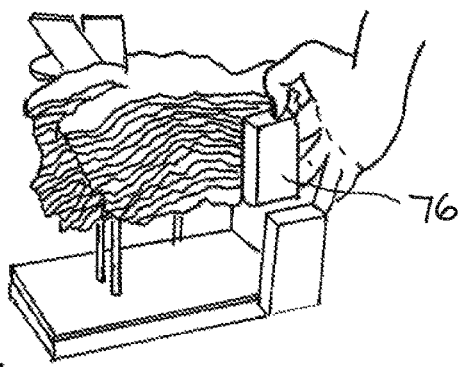
FIG. 16(d)

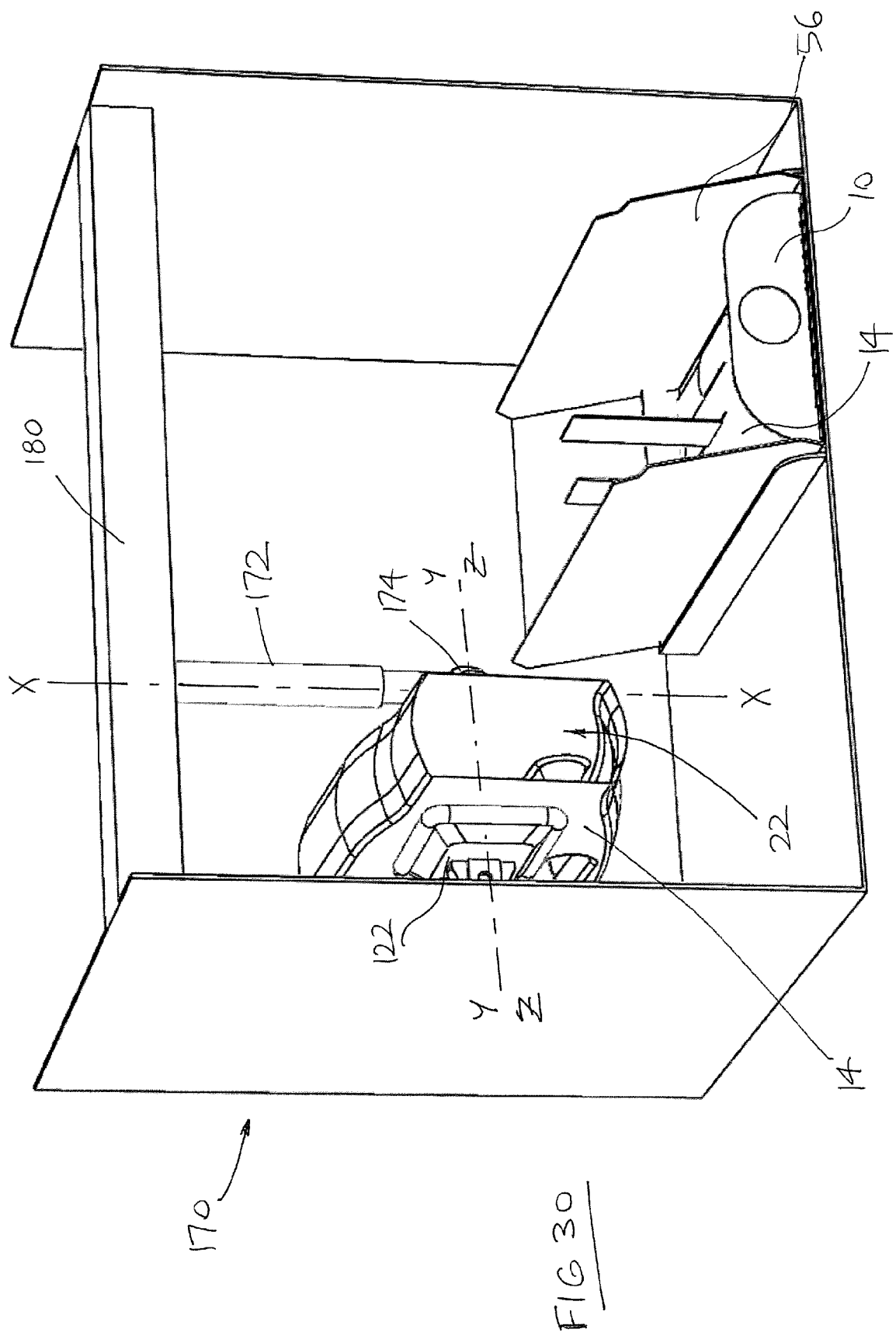

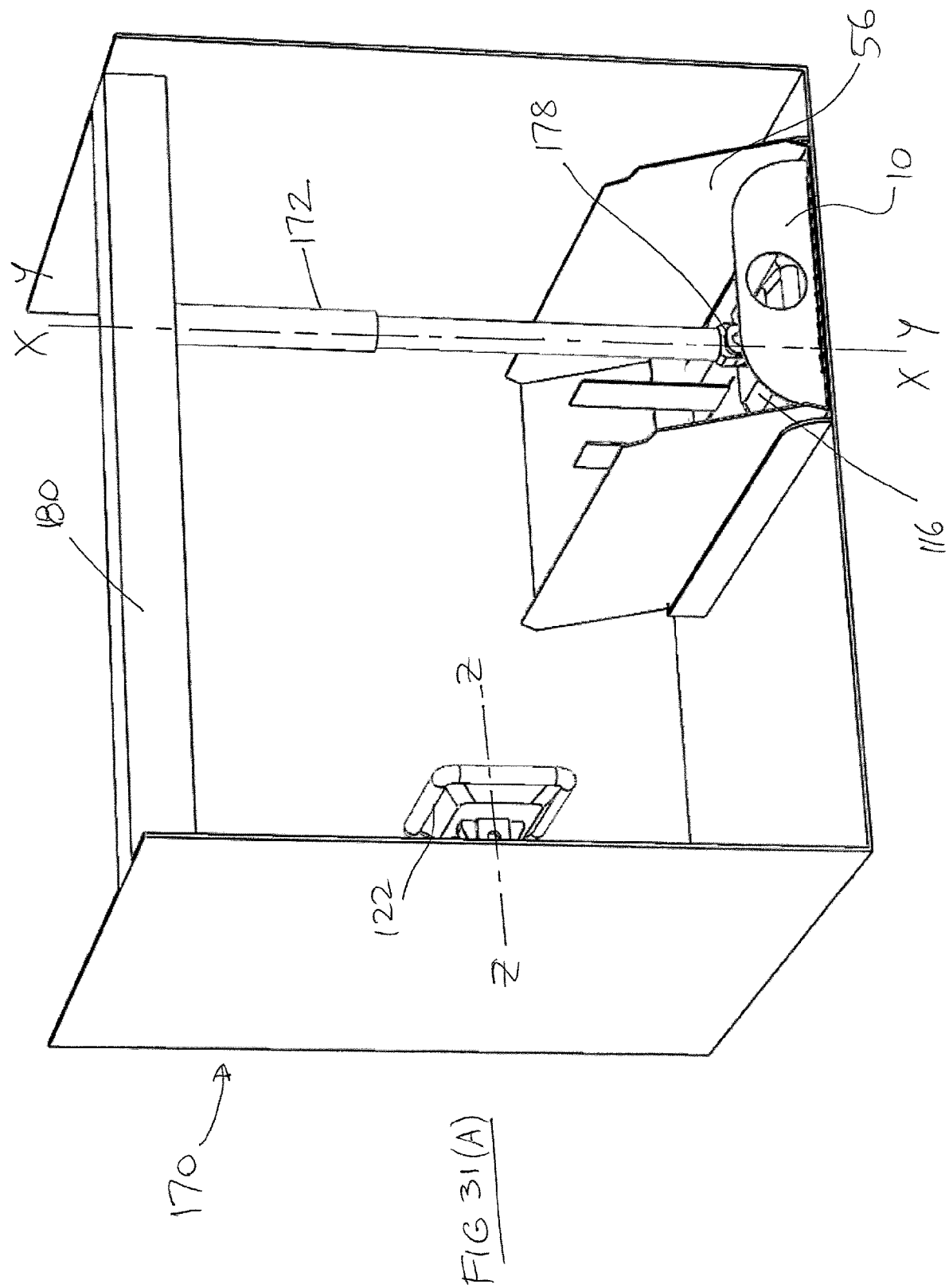

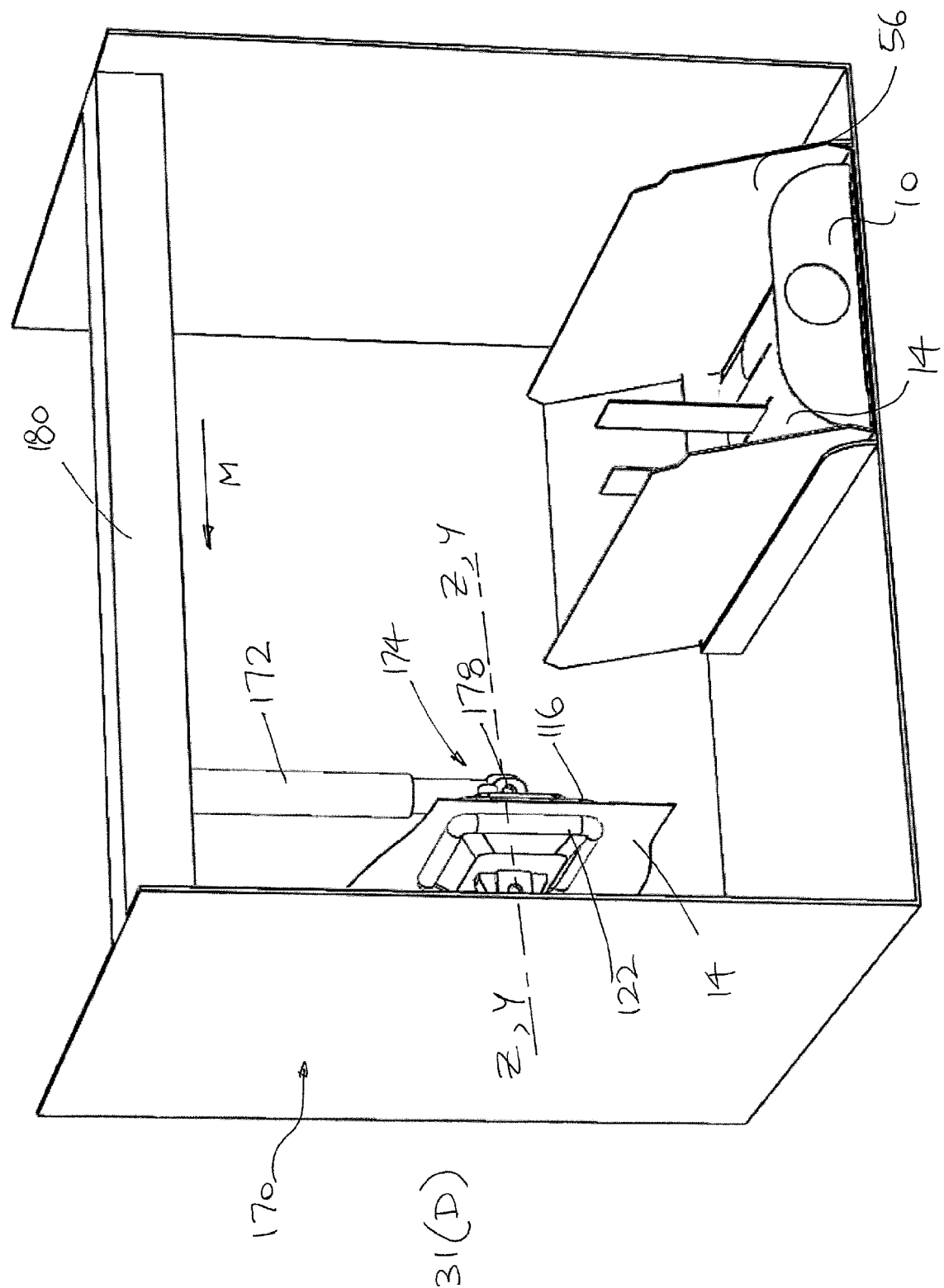

GLOVE DISPENSING CARTRIDGE, DISPENSING APPARATUS AND METHOD FOR USE THEREOF

TECHNICAL FIELD

This disclosure relates to a design of a cartridge for holding disposable gloves, and to glove dispensing apparatus, and to methods for use of the dispensing apparatus for fitting disposable gloves to the hands of a user in a hygienic manner.

BACKGROUND OF THE DISCLOSURE

The use of disposable gloves is common in many industries, such as food handling establishments where food such as sandwiches or the like may be prepared and sold to a customer, or other open food products such as meats are selected from a tray and wrapped for a customer to purchase. The use of such gloves is intended to improve hygiene and prevent the spread of germs which may take place if such food products are handled by bare hands. In other applications, disposable gloves are used by persons working in the medical and pharmaceutical industries, for example persons performing surgery, or doing medical research, where eliminating contamination (or cross-contamination) is paramount.

Disposable gloves are commonly sold in a box. A user pulls the gloves from an opening in the top of the box and subsequently applies them by hand. This requires the user to have significant contact with the exterior of the gloves prior to, and during, application of the gloves. As such, the outer surface of the glove can become contaminated with bacteria, dirt and/or other unwanted material present on the user's hands. In such situations, the person cannot simply pick up and 'pull on' some gloves using their hands, and expect that there will be no transfer of their own bacteria onto the exterior of the gloves which are intended for sterile use. Often more than one glove is removed at the same time from the box of new gloves, thereby creating waste. Additionally the process of putting on such gloves is slow.

An automated glove dispensing machine has been proposed in International Patent Application No. PCT/AU2008/001377 in the name of the present applicant. The machine includes a compartment for storing a roll of dispensable gloves, a moveable indexing arrangement for drawing a line of the gloves from the roll to a hand insertion station of the machine, and a glove opening device for opening the end glove of the line for insertion of a user's hand at the hand insertion station. The roll of gloves comprises a series of panels each comprising a disposable glove, where consecutive ones of the panels are joined together by a frangible connection. In use, the frangible connection is torn to separate the glove from the line as the user withdraws their hand from the hand insertion station.

However, it has become apparent that applications exist where a dispenser of freely separated, disposable gloves which are not frangibly joined to one another, and there is no possible contact between the exterior of a user's hand and the gloves located in the dispenser.

SUMMARY

In a first aspect, there is provided a cartridge for receiving a plurality of adjacent, aligned, disposable gloves, the cartridge comprising: a base; and a first element being arranged in use for alignment of the finger portions of the said plurality of gloves.

In some embodiments, the first element comprises one or more elongate strips, the or each strip being located in use between any two adjacent fingers of the respective glove(s). In one form, the first element comprises two elongate strips, each strip being located in use between two different adjacent fingers of respective glove.

In some embodiments, the or each elongate strip forms a part of the base, having frangible connections along two sides of the strip, wherein in use the or each strip is able to be hingedly deployed to extend from a remainder of the base once said frangible connections are broken, the strip(s) hingedly joined to the remainder of the base at one end of said strip(s). In some embodiments, the one or more elongate strips are of a pre-determined height at least equivalent to the maximum depth of the adjacent, aligned glove(s) when stacked on the base of the cartridge in use.

In some embodiments, the cartridge further comprises a second element arranged in use for alignment of a first portion of each of the said plurality of gloves.

In one form, the first portion of the said glove(s) is an open end of the glove(s), distal from the finger portions of the glove(s). In one particular embodiment, the second element comprises two raised portions, spaced apart from one another, and between which the respective open end of the or each glove is placed in use. In one form, the two raised portions are spaced apart by a length being generally the width of the open end of the glove(s). In some embodiments, the two raised portions extend from the base and are of a pre-determined height at least equivalent to the maximum depth of the adjacent, aligned glove(s) when stacked on the base of the cartridge in use.

In another form, the first portion of the said glove(s) is one or both of the left and right side edges of the glove(s) when laid flat. In one particular embodiment, the second element comprises two raised portions, spaced apart from one another by a length being generally the width between the left and right side edges of the glove(s) when laid flat. In some embodiments, the two raised portions extend from the base and are of a pre-determined height at least equivalent to the maximum depth of the adjacent, aligned glove(s) when stacked on the base of the cartridge in use.

In some embodiments, the cartridge is arranged in use to be received in a closure. In one form, the closure is a lidded box, sized so as to receive the base, and the first element when in the deployed position. In one particular embodiment, the base is arranged to be slidingly received into the closure. In an alternative embodiment, the cartridge forms part of a closure. In one form, the closure is a lidded box which includes the base, and sized to contain the first element when in the deployed position.

In a second aspect there is provided, in combination, a cartridge and a closure as defined in the first aspect, and a quantity of disposable gloves.

In a third aspect there is provided a method of positioning a plurality of adjacent, aligned, disposable gloves in a cartridge and above a base thereof, the method comprising the step of positioning each glove such that a finger portion is aligned in a proximal relationship with a first element of the cartridge, such that each respective glove is aligned in a stacked manner with an adjacent glove in the cartridge.

In some embodiments, the first element comprises one or more elongate strips, and the method comprises the step of locating the or each strip between any two adjacent fingers of the respective glove(s).

In some embodiments, the or each elongate strip is formed from a part of the base by the steps of breaking frangible connections arranged along two sides of said strip(s), and then hingedly deploying the strip(s) to extend from a remainder of the base by moving said strip(s) about an end thereof which is joined to the remainder of the base.

In some embodiments, the method comprises the step of locating one strip between two adjacent fingers of the or each respective glove, while simultaneously locating a second strip between a different two adjacent fingers of the or each respective glove. In some other embodiments, the method comprises the step of locating one strip between two adjacent fingers of the or each respective glove, while simultaneously locating a second strip between one of the said two adjacent fingers and a third finger of the or each respective glove.

In some embodiments, the method further comprises the step of positioning each glove such that a first portion of the glove is aligned with a second element of the cartridge; and wherein each respective glove is aligned in a stacked manner with an adjacent glove in the cartridge by its proximal relationship to the first and second elements.

In some embodiments, the first portion of the said glove(s) is an open end of the glove(s), distal from the finger portion of the glove(s). In one form, the second element comprises two raised portions which extend from the base, and are spaced apart from one another by a length being generally the width of the open end of the glove(s), and the method comprises the step of placing the respective first portion of the glove(s) between the two raised portions.

In some other embodiments, the first portion of the said glove(s) is one or both of the left and right side edges of the glove(s) when laid flat. In some embodiments, the second element comprises two raised portions which extend from the base, and are spaced apart from one another by a length being generally the width of between the left and right side edges of the glove(s) when laid flat, and the method comprises the step of placing the respective glove(s) between the two raised portions.

In some embodiments, the method further comprises the step of either locating the cartridge in a closure, or forming a closure around the cartridge if the cartridge itself forms a part of a closure. In some embodiments, the method further comprises the step of sealing the closure.

In a fourth aspect, there is provided a cartridge for receiving a plurality of adjacent, aligned, disposable gloves, the cartridge comprising: a base; and a first element being arranged in use for alignment of a first portion of each of the said plurality of gloves.

In some embodiments, the first portion of the said glove(s) is an open end of the glove(s), distal from the or each finger portions of the glove(s). In one embodiment, the first element comprises two raised portions, spaced apart from one another, and between which the respective open end of the or each glove is placed in use. In one form, the two raised portions are spaced apart by a length being generally the width of the open end of the glove(s). In some embodiments, the two raised portions extend from the base and are of a pre-determined height at least equivalent to the maximum depth of the adjacent, aligned gloves when stacked on the base of the cartridge in use.

In some other embodiments, the first portion of the said glove(s) is one or both of the left side and right side edges of the glove(s) when laid flat. In one embodiment, the first element comprises two raised portions, spaced apart from one another by a length being generally the width between the left side and right side edges of the glove(s) when laid flat. In some embodiments, the two raised portions extend from the base and are of a pre-determined height at least equivalent to the maximum depth of the adjacent, aligned glove(s) when stacked on the base of the cartridge in use.

In some embodiments, the cartridge further comprises a second element arranged in use for alignment of the finger portions of the said plurality of gloves. In one form, the second element comprises one or more elongate strips, the or each strip being located in use between any two adjacent fingers of the respective glove(s). In one form of this the second element comprises two elongate strips, when deployed each strip being located between two different adjacent fingers of the respective glove(s). In some embodiments, the or each elongate strip forms a part of the base, having frangible connections along two sides of the strip, wherein in use the or each strip is able to be hingedly deployed to extend from a remainder of the base once said frangible connections are broken, the strip(s) hingedly joined to the remainder of the base at one end of said strip(s). In some embodiments, the one or more elongate strips are of a pre-determined height at least equivalent to the maximum depth of the adjacent, aligned glove(s) when stacked on the base of the cartridge in use.

In some embodiments, the cartridge is arranged in use to be received in a closure. In one form, the closure is a lidded box, sized so as to receive the base, and the first element when in the deployed position. In one particular embodiment, the base is arranged to be slidingly received into the closure. In an alternative embodiment, the cartridge forms part of a closure. In one form, the closure is a lidded box which includes the base, and sized to contain the first element when in the deployed position.

In a fifth aspect, there is provided, in combination, a cartridge and a closure as defined in the fourth aspect, and a quantity of disposable gloves.

In a sixth aspect, there is provided a method of positioning a plurality of adjacent, aligned, disposable gloves in a cartridge and above a base thereof, the method comprising the step of positioning each glove such that a first portion is aligned in a proximal relationship with a first element of the cartridge, such that each respective glove is aligned in a stacked manner with an adjacent glove in the cartridge.

In some embodiments of the method, the first portion of the said glove(s) is an open end of the glove(s), distal from the finger portion of the glove(s). In one form, the first element comprises two raised portions which extend from the base, and are spaced apart from one another by a length being generally the width of the open end of the glove(s), and the method comprises the step of placing the respective first portion of the glove(s) between the two raised portions.

In other embodiments of the method, the first portion of the said glove(s) is one or both of the left side and right side edges of the glove(s) when laid flat. In one form, the first element comprises two raised portions which extend from the base, and are spaced apart from one another by a length being generally the width of between the left and right side edges of the glove(s) when laid flat, and the method comprises the step of placing the respective glove(s) between the two raised portions.

In some embodiments, the method further comprises the step of positioning each glove such that the finger portion of the glove(s) is aligned with a second element of the cartridge; and wherein each respective glove is aligned in a stacked manner with an adjacent glove in the cartridge by its proximal relationship to the first and second elements.

In one form of the method in which the second element comprises one or more elongate strips, the method comprises the step of locating the or each strip between any two adjacent fingers of the respective glove(s). In one form of this, the or each elongate strip is formed from a part of the base by the step of breaking frangible connections arranged along two sides of said strip(s), and then hingedly deploying the strip(s) to extend from a remainder of the base by moving said strip(s) about an end thereof which is joined to the remainder of the base. In one arrangement, the method comprises the step of locating one strip between two adjacent fingers of the or each respective glove, while simultaneously locating a second strip between a different two adjacent fingers of the or each respective glove. In an alternative arrangement, the method comprises the step of locating one strip between two adjacent fingers of the or each respective glove, while simultaneously locating a second strip between one of the said two adjacent fingers and a third finger of the or each respective glove.

In some embodiments, the method further comprises the step of either locating the cartridge in a closure, or forming a closure around the cartridge if the cartridge itself forms a part of the closure. In some embodiments, the method further comprises the step of sealing the closure.

In a seventh aspect there is provided a method of supporting a plurality of adjacent, aligned, disposable gloves, the method comprising the steps of: frictionally interfitting a planar element in the open end of each glove; and positioning the said gloves such that the planar element which is fitted into the or each glove(s) is in contact with a first element which extends from a cartridge; wherein the or each glove is supported in an aligned manner by the positional relationship of the planar element and the first element.

In some embodiments, the method further comprises the step of positioning the or each glove such that a finger portion of the gloves is aligned with a second element which extends from the cartridge. In one embodiment, the second element comprises one or more elongate strips, and the method comprises the step of locating the or each strip between any two adjacent fingers of respective gloves.

In one form, the method comprises the step of locating one strip between two adjacent fingers of the or each respective glove, while simultaneously locating a second strip between a different two adjacent fingers of the or each respective glove. In an alternative form, the method comprises the step of locating one strip between two adjacent fingers of the or each respective glove, while simultaneously locating a second strip between one of the said two adjacent fingers and a third finger of the or each respective glove.

In some embodiments, the method further comprises the step of removing the planar element from the or each glove.

In some embodiments, the method further comprises the step of either locating the cartridge in a closure, or forming a closure around the cartridge if the cartridge itself forms a part of the closure. In one form, the method further comprises the step of sealing the closure.

In an eighth aspect, there is provided a machine arranged for dispensing a disposable glove, the machine comprising: an articulated arm arranged in use for contacting and retaining a first part of the glove and for moving said glove from a first position in which the glove is located in a cartridge containing one or more gloves, to a second position in which a second part of the said glove is able to be contacted with and retained by an anchoring means, wherein, once in the second position, one or both of the articulated arm or anchoring means is moveable in a direction relative the other, in use so as to stretch the glove sufficiently wide at an open end thereof to enable admission of a human hand.

In some embodiments of the machine, the articulated arm moves pivotally as it moves the glove to the second position. In one form of this, the articulated arm moves pivotally about a mounting point which is located at an interior wall of the machine. In some embodiments, the anchoring means is arranged at a support arm, which itself is moveable so as to move the anchoring means into the second position. In some embodiments, the support arm is elongate, and is moveable in an axial direction along its length, both toward and away from the articulated arm. In one form of this, the support arm is telescopic.

In some other embodiments of the machine, the articulated arm is elongate, and is moveable in an axial direction along its length, both toward and away from the cartridge. In some embodiments of this, after the glove has been moved from the first position, the cartridge is laterally moveable out of alignment with the axial direction of movement of the articulated arm. In one form, said lateral movement of the cartridge exposes the anchoring means, the anchoring means being located in alignment with the axial direction of movement of the articulated arm. In some embodiments, further movement of the articulated arm along its said axial direction of movement and towards the anchoring means shall move said glove into the second position.

In some further embodiments of the machine, a head region of the articulated arm is joined to and pivotable about the axis of the articulated arm, to enable the head region to be aligned with the orientation of the glove when the glove is in the first position, as part of moving the said glove away from the first position. In some embodiments, the head region of the articulated arm is fitted with an alignment sensing device to enable the head region to be aligned with a physical feature of the glove, to improve contact with and retention of the glove at the articulated arm.

In some embodiments of this, the articulated arm is elongate, and is moveable in an axial direction along its length, one such movement being away from the cartridge, as part of moving the said glove away from the first position. In some embodiments, the elongate articulated arm is telescopically moveable in the axial direction along its length. In some embodiments, an axis of the head region of the articulated arm is further rotatable into an orientation which not aligned with the axial direction of movement of the elongate articulated arm, for purposes of at least one of: (i) enabling the head region to be aligned with the orientation of the glove when the glove is in the first position, for moving the glove away from the first position, and (ii) moving the glove towards the second position.

In one form of this, the axis of the head region is rotatable so as to be in alignment with an axis of orientation of the anchoring means, as part of moving said glove toward the second position. In some embodiments, the articulated arm and head region is also arranged to be moveable in a direction towards the anchoring means, in order to move said glove into the second position and be contacted with the anchoring means.

In some embodiments, the contact and retention of the glove at the articulated arm, or if applicable at a head region of the articulated arm, is by means of a suction device, which uses air pressure to retain the respective first or second side of a glove thereto. In one form of this, the contact and retention of the glove at the anchoring means is by means of a suction device, which uses air pressure to retain the other of the respective first or second side of a glove thereto.

In some embodiments, the suction device comprises at least one suction cup or suction hole arranged at a support surface. In some embodiments, a plurality of suction cups or suction holes are arranged in an array at the support surface in locations which align with the palm and the thumb region of a glove. In some other embodiments, the suction cups or suction holes are further arranged in an array at the support surface in locations which align with the fingers of a glove.

In some embodiments, the first part of the glove is one of the group comprising a palmar side of the glove and a dorsal side of the glove, and the second part of the glove is the respective other one of the group comprising the palmar side and the dorsal side.

In a ninth aspect there is provided a method for dispensing a disposable glove, the method comprising the steps of: moving an articulated arm to contact and retain a first part of the glove which is located in a first position located in a cartridge; moving said glove out of the cartridge toward a second position, in which a second part of the said glove is able to be contacted with and retained by an anchoring means; and wherein once in the second position, the step of moving one or both of the articulated arm or anchoring means in a direction relative the other, in use so as to stretch the glove sufficiently wide at an open end thereof to enable admission of a human hand.

In some embodiments of the method, the step of contacting and retaining the glove when in the first position at the articulated arm is achieved by the step of activation of a suction device.

In some embodiments of the method, the step of moving the glove toward the second position is achieved by activation of the movement of the articulated arm to cause it to pivot, or to cause it to move in a direction along its axial length. In some embodiments, movement of the anchoring means is achieved by the step of activation of an articulated arm.

In some other embodiments, the method further includes the step of slidingly moving the cartridge in relation to the articulated arm. In some embodiments, the step of slidingly moving the cartridge exposes an anchoring means.

In some further embodiments of the method, the step of moving an articulated arm to contact and retain a first part of the glove further includes pivoting a head region of the articulated arm about the axis of the articulated arm so as to align the head region with the glove, this step guided by an alignment sensing device to detect a physical feature of the glove.

In some embodiments, moving the glove into the second position where a second part of the said glove is able to be contacted with and retained by an anchoring means includes the step of rotation of an axis of the head region of the articulated arm which is carrying said glove into alignment with an axis of orientation of the anchoring means. In some embodiments, moving the glove into the second position where a second part of the said glove is in contact with and retained by the anchoring means comprises the step of moving the articulated arm and head region in a direction towards the anchoring means.

In some embodiments of any of these methods, the contact and retention of the glove in the second position at the anchoring means is achieved by the step of activation of a suction device.

In a tenth aspect, the machines as herein defined for dispensing disposable gloves may also further comprise at least one ultra-violet (UV) light source arranged within a housing of the machine for treating the gloves with ultra-violet light.

In one embodiment, there is provided an apparatus for dispensing gloves, comprising at least one ultra-violet (UV) light source arranged within a housing of the apparatus for treating the gloves with ultra-violet light.

In some embodiments, the housing includes a cover, and the UV light source is operable for treating the gloves when the cover of the housing is closed.

In some embodiments, the UV light source is mounted within the housing of the glove dispensing apparatus whereby the duration of operation of the UV light source is controlled by a control system which may only actuate when the user's hand is withdrawn from the machine.

Typically, the cartridge of gloves in a closure or package of disposable gloves as described herein, is a set of freely separated gloves which are not frangibly joined to one another. A package of disposable gloves of this type may be provided or utilised in a glove dispensing apparatus in which the gloves are arranged in a stacked fashion on top of one another, so as to be able to be consecutively withdrawn from the cartridge of gloves in use.

Such gloves may be a "non-handed" glove that can be worn on either the right or left hand of the use (that is, the same glove can be worn on either the right or the left hand of the user), or of the "handed" type, and dispensed by the aforementioned method as the user inserts each hand into a respective glove with their hand in a "thumb up" orientation when the gloves are presented by the delivery apparatus in a corresponding vertical orientation with the opened cuff of the glove facing the user, allowing for ease of donning of the gloves. (The "thumb" of a glove is meant that end finger of the glove for receiving, or which is arranged to receive, the thumb of the user's hand).

Advantageously, the opening and presentation of the gloves by embodiments of glove dispensing apparatus as described herein may reduce or prevent contamination of outer surface(s) of the gloves which may otherwise occur when it is necessary for the user to handle the glove with their other bare hand as with the convention donning of gloves. The gloves being dispensed may be a loose fitting lightweight "sandwich" type of glove suitable for use by persons working in food related industries or in delicatessens, sandwich bars, confectionary shops or the like where it is necessary to regularly don gloves for short periods when handling food whilst serving a customer and then remove and dispose of them to collect payment from the customer. However, a more likely application for the delivery equipment of the present disclosure is for gloves used by persons working in the medical and pharmaceutical industries, for example persons performing surgery, or doing medical research, where eliminating contamination (or cross-contamination) is paramount. In such situations, the person cannot simply pick up and 'pull on' some gloves using their hands, and expect that there will be no transfer of their own bacteria onto the exterior of the gloves which are intended for sterile use.

Advantageously also, the glove dispensing apparatus in one or more embodiments as described herein may provide for relatively fast donning of gloves, and can avoid the use of single, loose gloves in a box which can otherwise become tangled together resulting in wastage in the event a number of gloves are drawn from the box together.

Other aspects, features, and advantages will become further apparent from the following detailed description when read in conjunction with the accompanying drawings which are a part of this disclosure and which illustrate, by way of example, principles of the inventions disclosed.

DESCRIPTION OF THE FIGURES

The accompanying drawings facilitate an understanding of the various embodiments.

FIG. 15(a) shows a perspective view of the cartridge of FIG. 13, along with a perspective view of an embodiment of a cartridge support into which the cartridge can be lowered, in use for supporting the cartridge during filling with disposable glove(s);

FIG. 15(b) shows a perspective view of the cartridge and cartridge support of FIG. 15(a), where the cartridge is lowered into the cartridge support and is ready for filling with disposable glove(s);

FIG. 16(a) shows a perspective view of a further embodiment of a cartridge support into which the cartridge can be lowered, in use for supporting the cartridge during filling with disposable glove(s);

FIG. 16(b) shows a side elevation view of the cartridge of FIG. 13 and the cartridge support of FIG. 16(a), where the cartridge is lowered into the cartridge support and is filled with disposable glove(s);

FIG. 16(c) shows a perspective, end elevation view of the cartridge, the cartridge support and the gloves shown in FIG. 16(b);

FIG. 16(d) shows a perspective, side elevation view of the cartridge and the cartridge support of FIG. 16(b), where the cartridge which is filled with disposable glove(s) is being raised and removed from the cartridge support;

Figure 28:
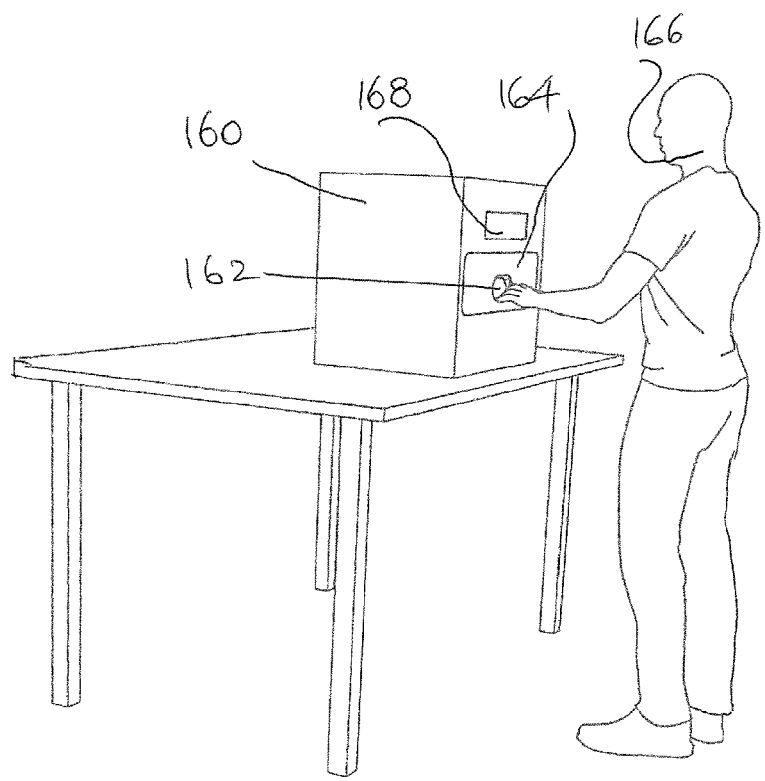
Figure 29:
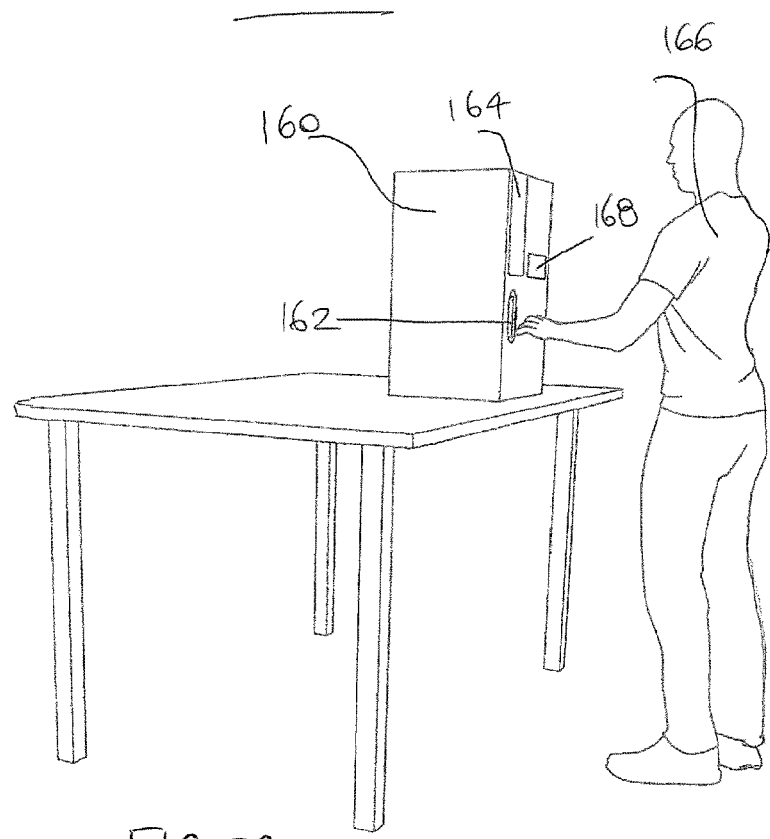
Figure 31B:
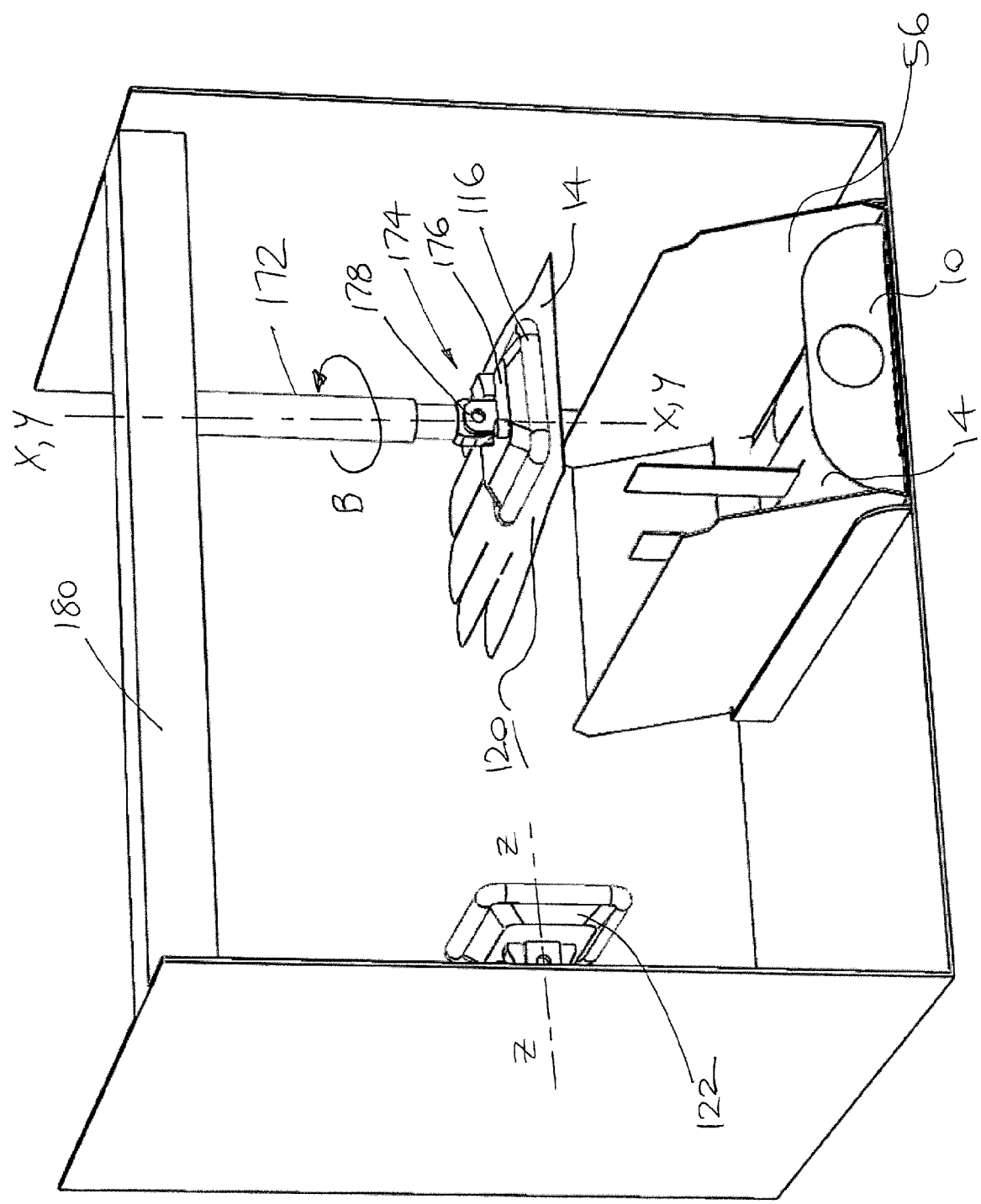
Figure 31C:
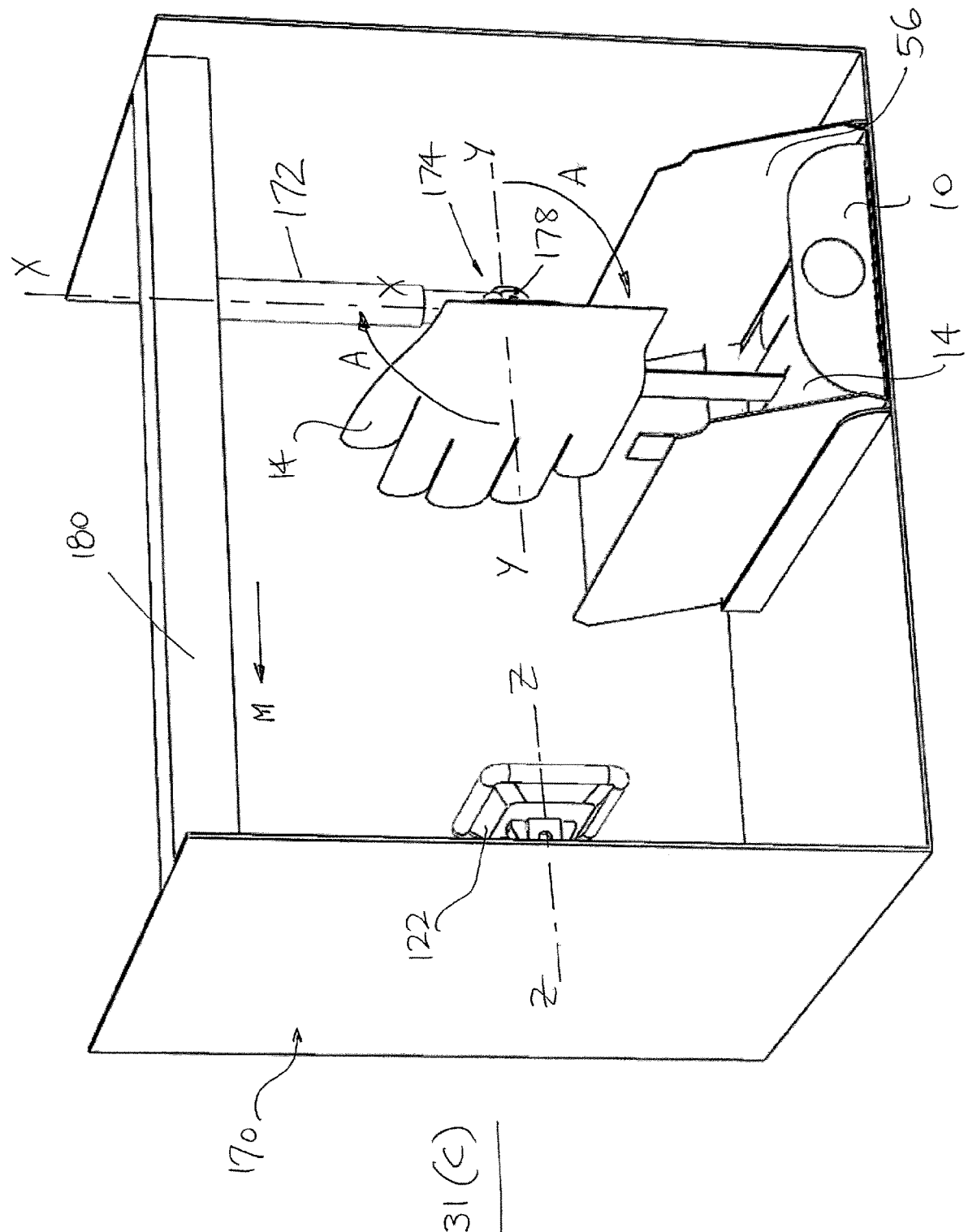
Figure 31E:
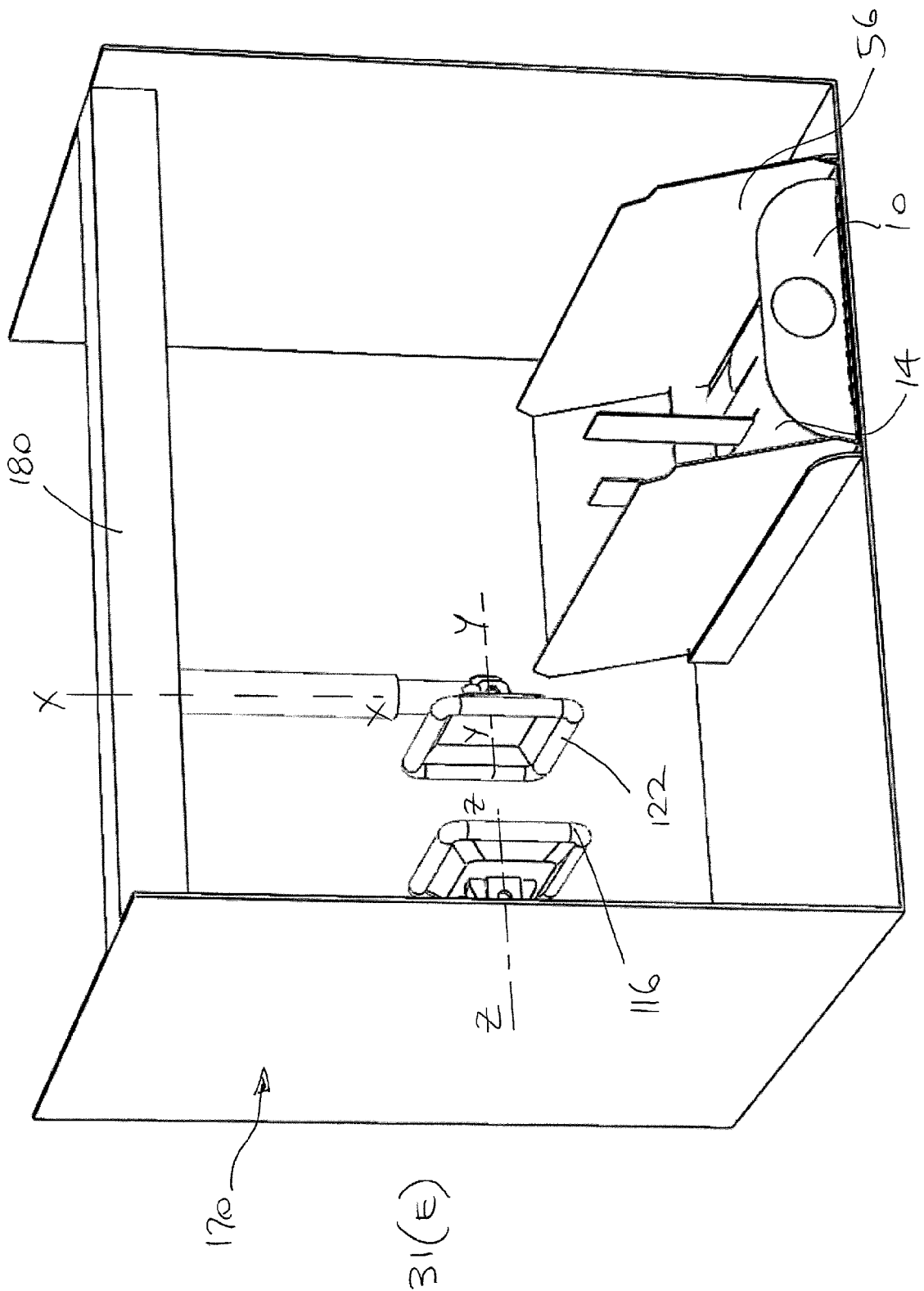

27(b) showing the mechanism attached to the disposable glove in an expanded configuration, to open that glove for the entry of a user's hand;

FIG. 28 shows a perspective, schematic view of an embodiment of a glove dispensing machine in accordance with the present disclosure, when in use by an operator; and FIG. 29 shows a perspective, schematic view of a further embodiment of a glove dispensing machine in accordance with the present disclosure, when in use by an operator.

Figure 32:
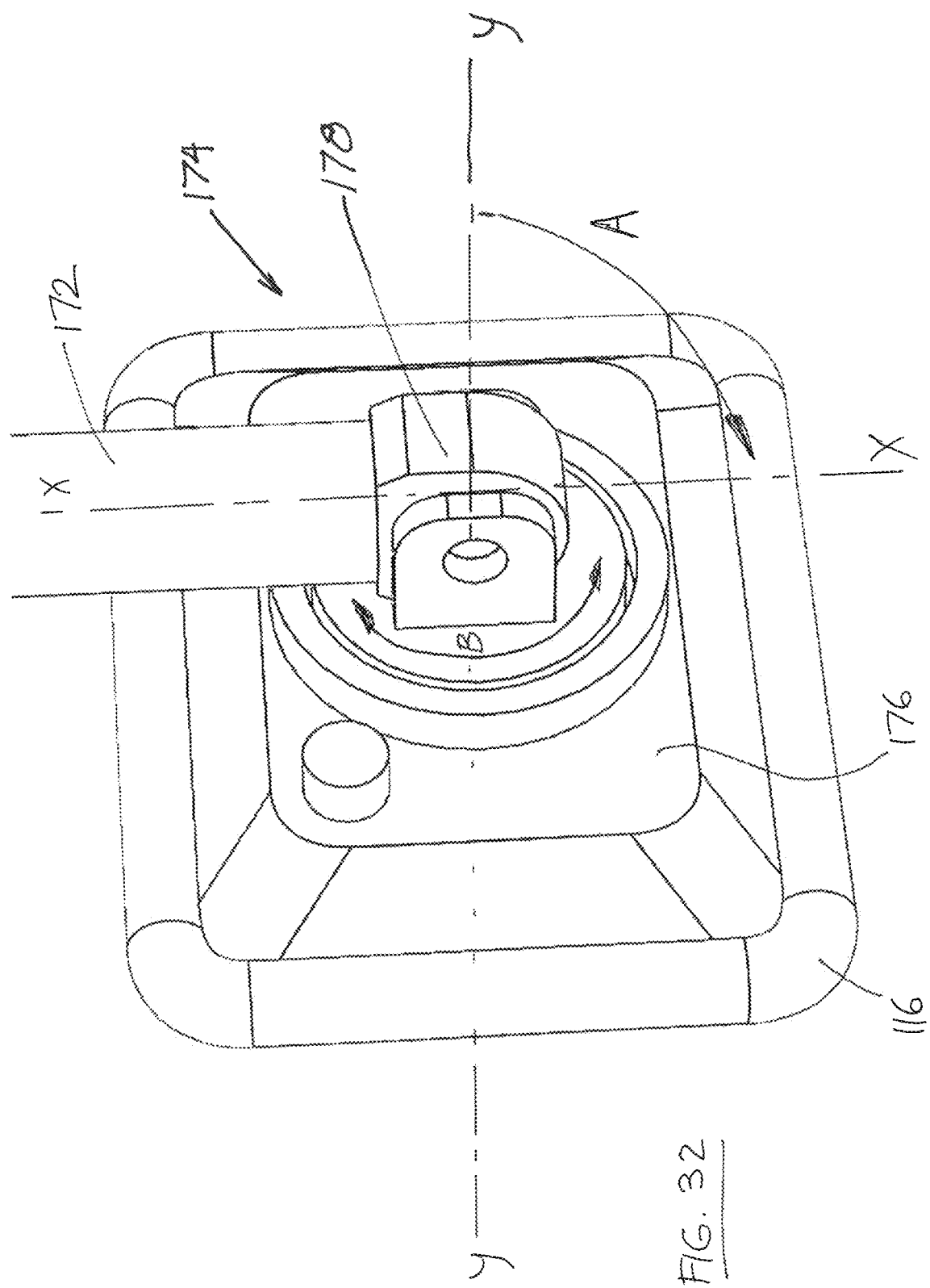
Figure 33:
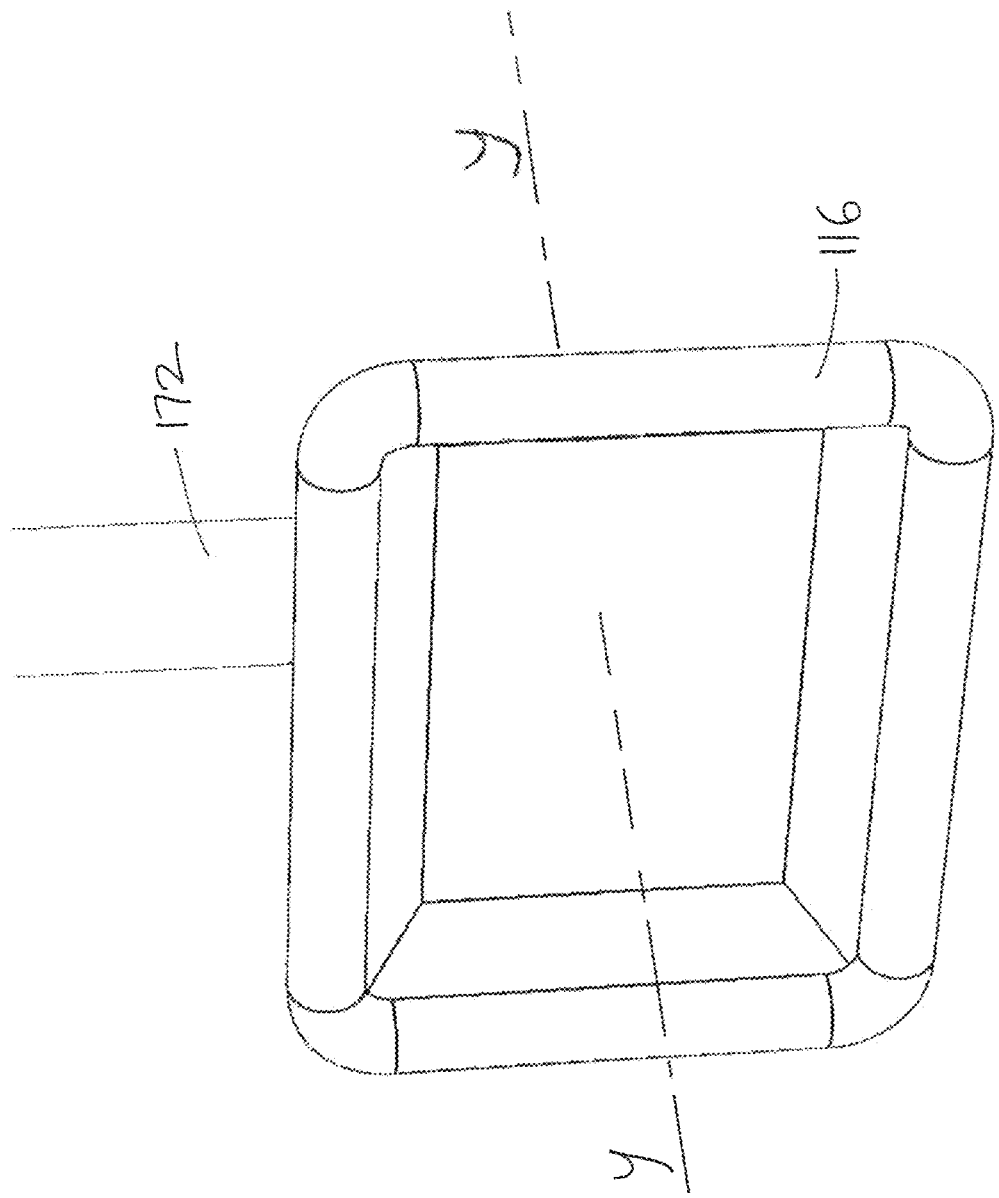
Figure 34:
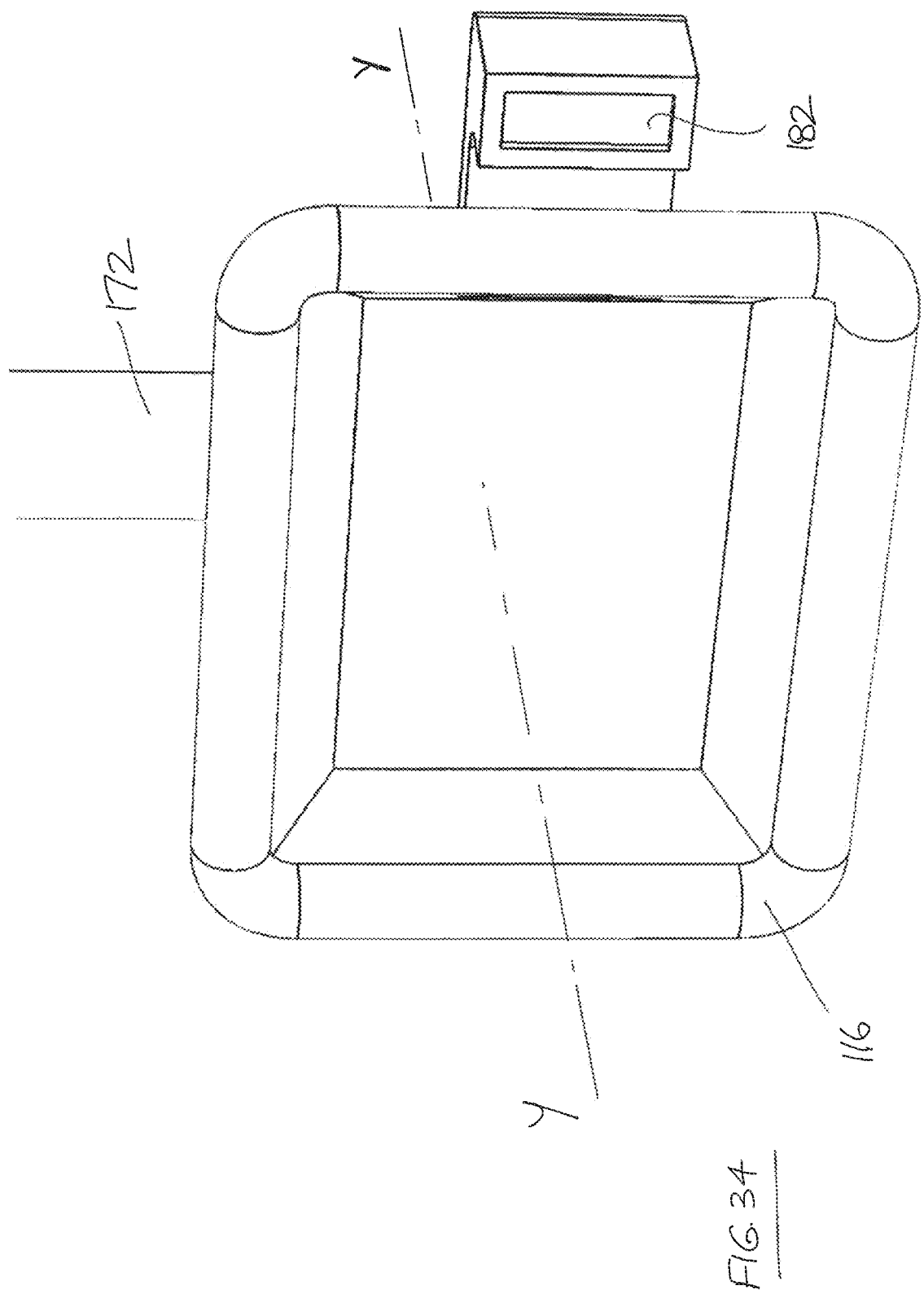
Figure 35:
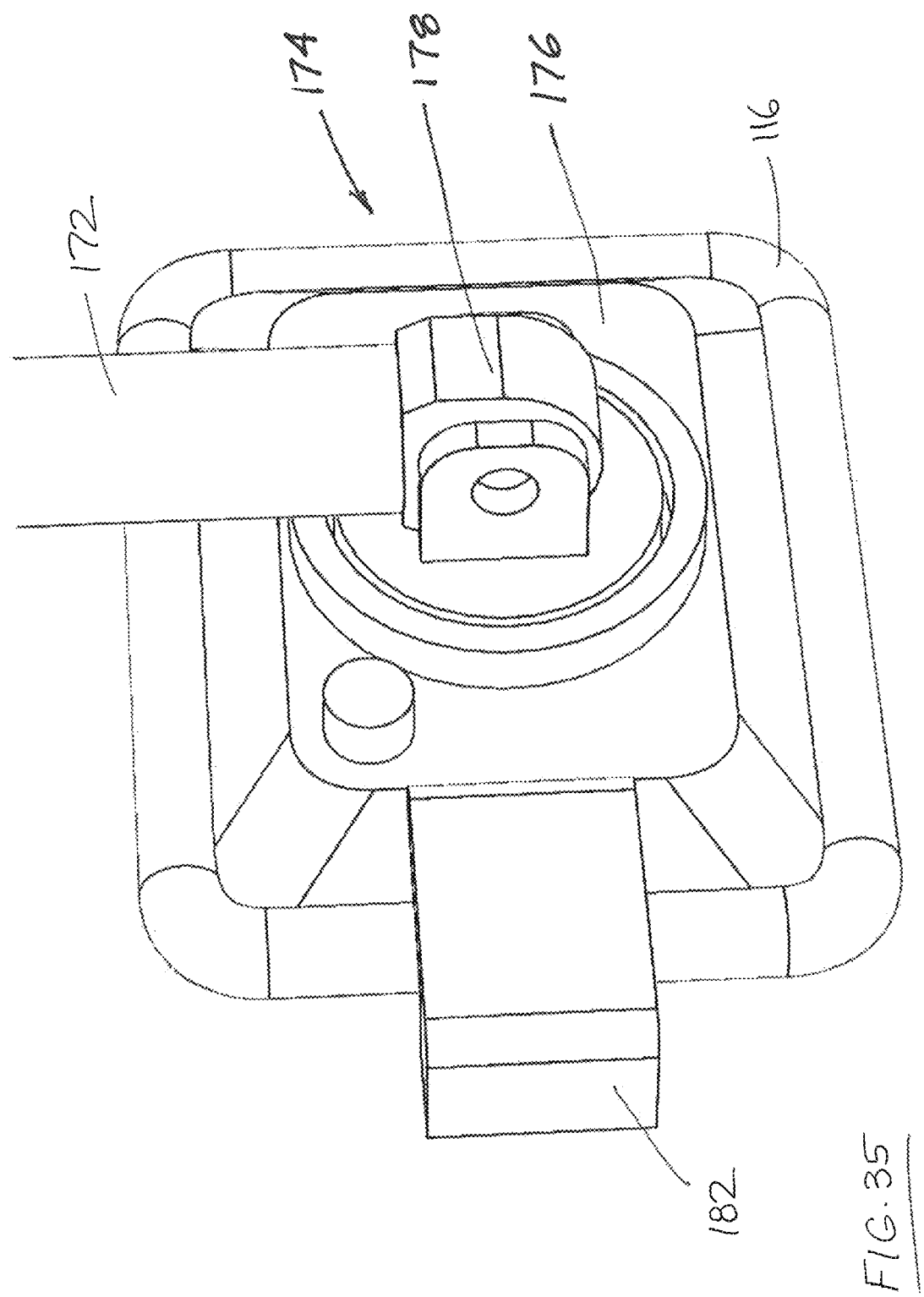
Figure 36:
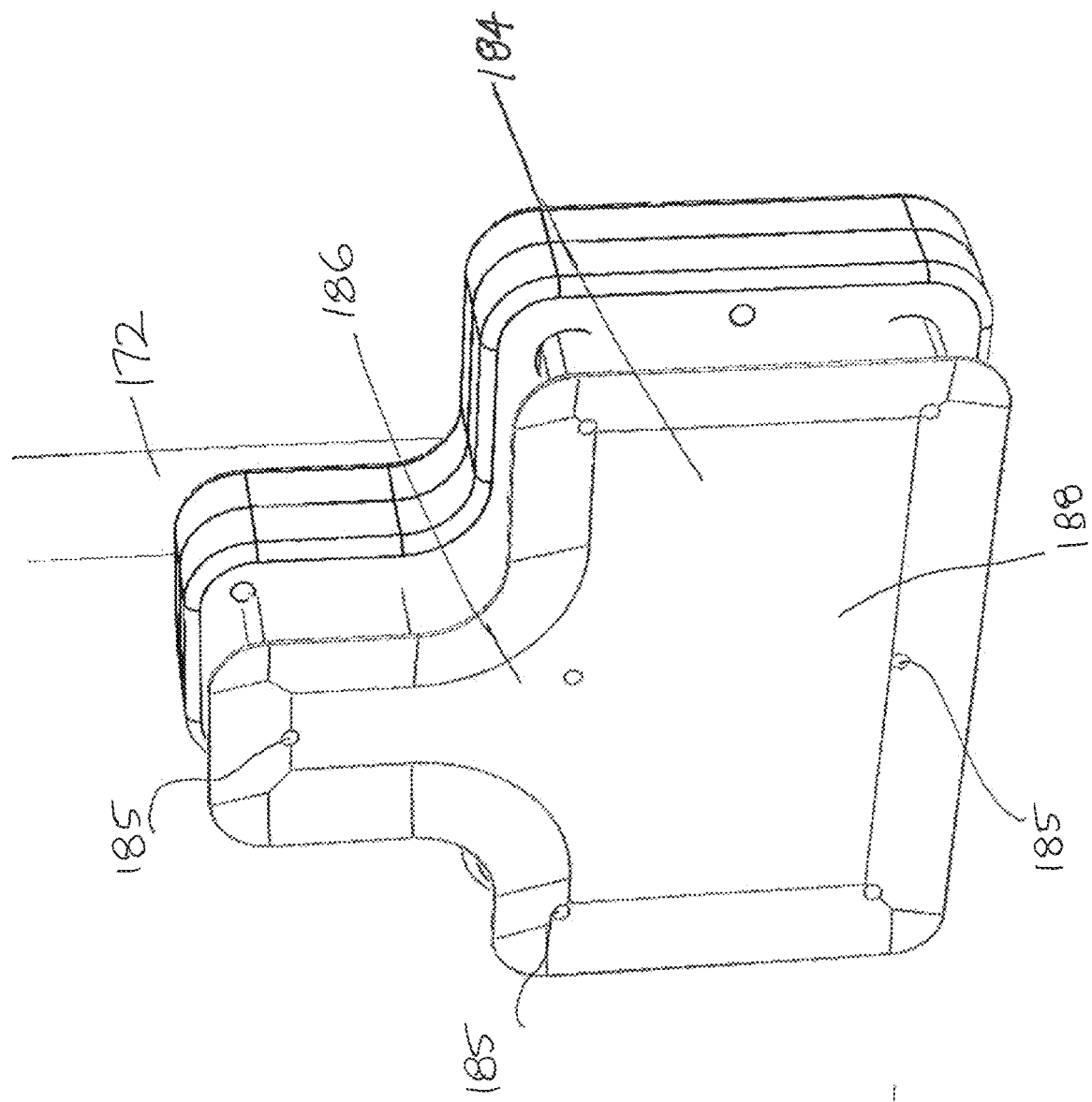
Figure 37:
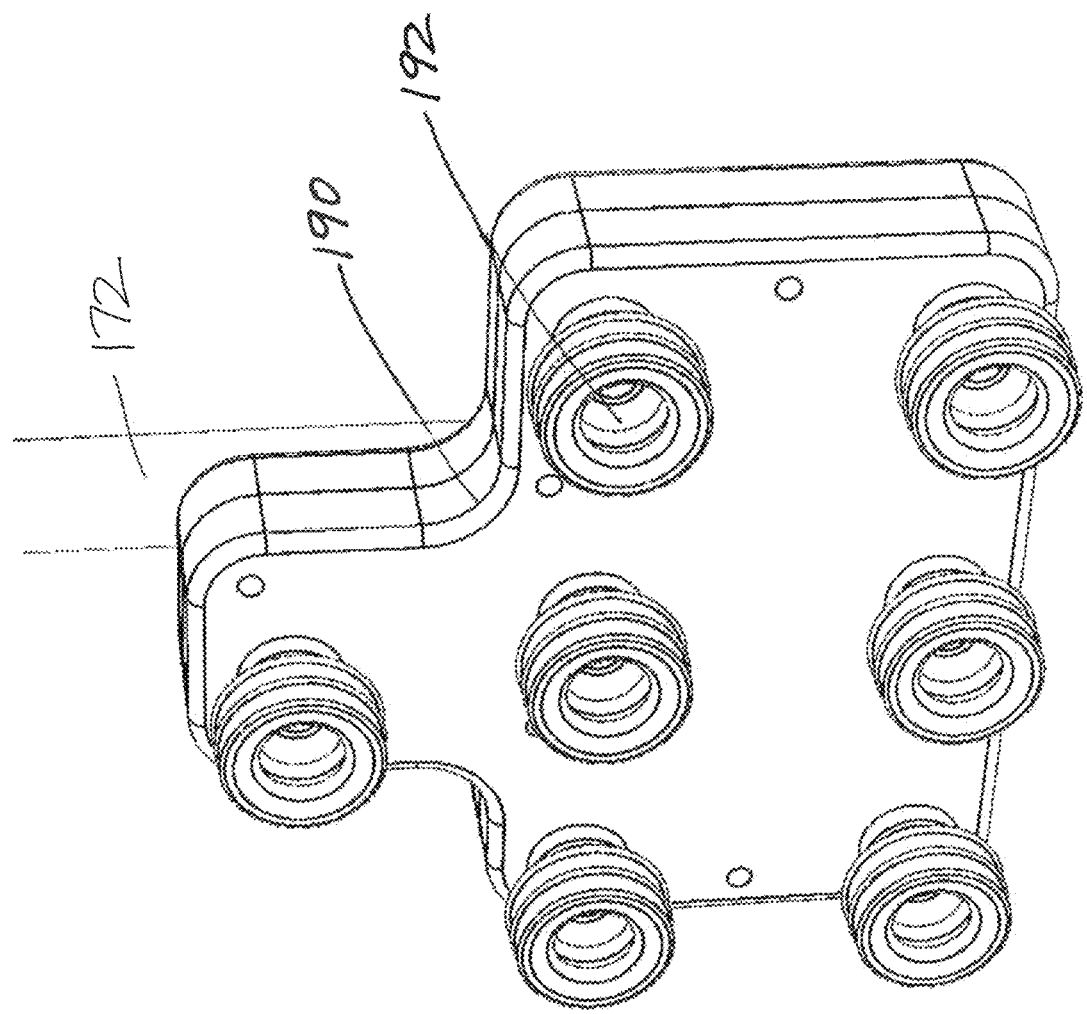
Figure 38:
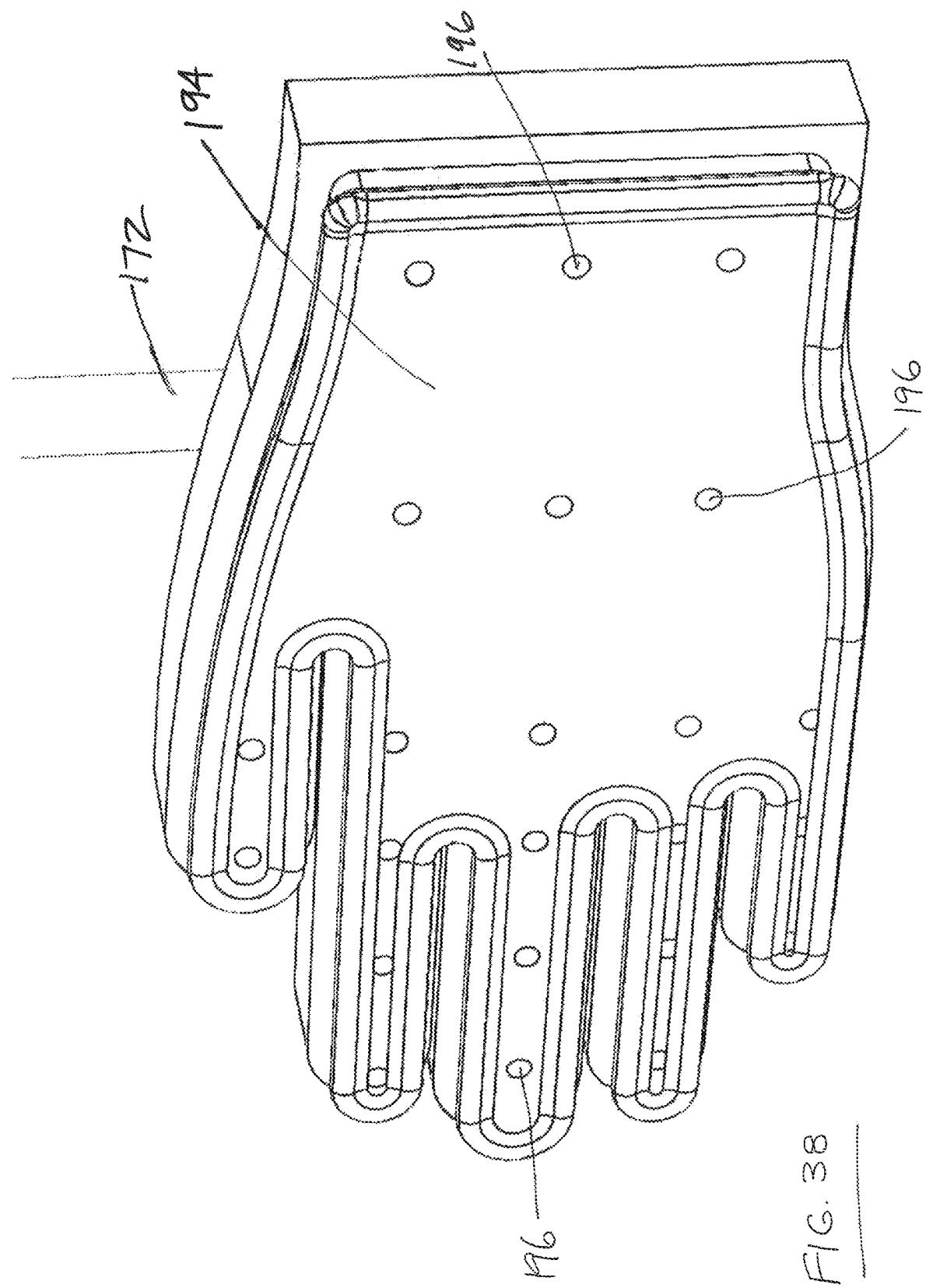

FIG. 30 shows a perspective, schematic view of a further embodiment of a glove dispensing machine in accordance with the present disclosure, with a disposable glove shown in an open position;

FIGS. 31(a), 31(b), 31(c), 31(d) and 31(e) show a sequence of steps of how the machine of FIG. 30 is able to select a disposable glove and to open that glove for the entry of a user's hand;

FIG. 32 shows a perspective, schematic view of a portion of the articulated arm of the machine of FIG. 30, showing more detail of the pivotable and rotatable head region and of the back of the suction device which is located thereat;

FIG. 33 shows a perspective view of the articulated arm of the machine of FIG. 32, showing more detail of the front of the suction device located at the pivotable and rotatable head region thereof;

FIG. 34 shows a perspective, schematic view of a further embodiment of a suction device located at the pivotable and rotatable head region of an articulated arm of a glove dispensing machine in accordance with the present disclosure, the head region being fitted with an alignment sensing device located adjacent to the suction device;

FIG. 35 shows a perspective view of the articulated arm of the machine of FIG. 34, showing more detail of the front of the pivotable and rotatable head region and of the back of the suction device and the alignment sensing device which is located thereat;

FIG. 36 shows a perspective, schematic view of a further embodiment of a suction device located at the pivotable and rotatable head region of an articulated arm of a glove dispensing machine in accordance with the present disclosure;

FIG. 37 shows a perspective, schematic view of a further embodiment of a suction device located at the pivotable and rotatable head region of an articulated arm of a glove dispensing machine in accordance with the present disclosure; and FIG. 38 shows a perspective, schematic view of a further embodiment of a suction device located at the pivotable and rotatable head region of an articulated arm of a glove dispensing machine in accordance with the present disclosure;

DETAILED DESCRIPTION

This disclosure relates to the features of a cartridge for receiving a plurality of disposable gloves for use on a user's hands. In the embodiments disclosed, the gloves are stacked in an aligned manner in the cartridge, that is, like gloves oriented in the same direction. Typically, the cartridge and any associated closure therearound are aftermarket consumable items which find particular use with the various embodiments of machines for dispensing the gloves, as shall be herein described.

Turning to the Figures, in the exemplary embodiments shown, the cartridge 10 comprises a rectangular-shaped, flat base panel 12, which is at least as wide as a glove 14 laid flat thereon (a width from the thumb side 16 to the pinkie finger side 18), and at least as long as a glove 14 laid flat thereon (a length from the tip 20 of the middle finger to the cuff 22 of the glove 14). Two rectangular, elongate strip portions 24, 26 being a part of the panel 12 are partially separable from the body of the remainder of the panel 12 along two parallel, frangible score lines, so as to each be able to be deployed by being folded in a hinged manner into a respective, upwardly oriented strip 24, 26, and to lie transverse of the cartridge panel 12. Both strips 24, 26 remain joined to the remainder of the cartridge panel 12 at the hinge line, so that detachment from the panel 12 does not occur in normal use. As shown in each of the Figures, the strips 24, 26 have parallel sides 28, 30, for ease of detachment from the remainder of the cartridge panel 12, although in other embodiments it is possible that the strips are of a different shape (for example, with two sides which taper toward one another).

Figure 1:
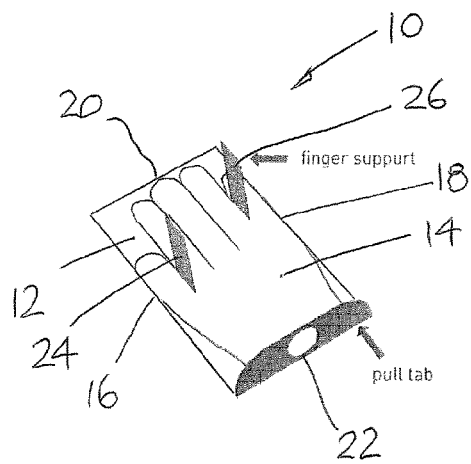
FIG. 1 shows a perspective view of a cartridge in accordance with a first embodiment of the present disclosure, with a disposable glove located at the cartridge.
Figure 2:
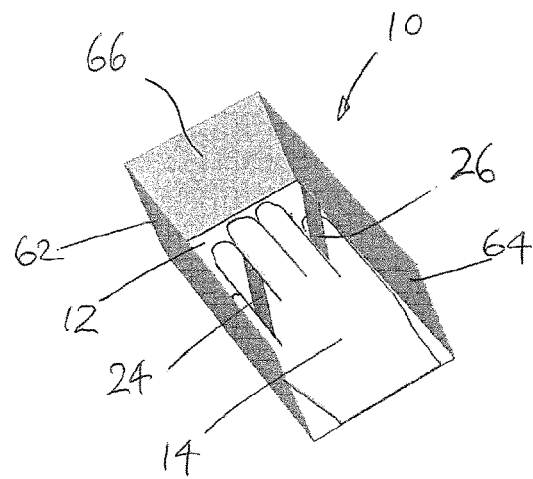
FIG. 2 shows a perspective view of a cartridge in accordance with a further embodiment of the present disclosure, with a disposable glove located at the cartridge.
Figure 5:
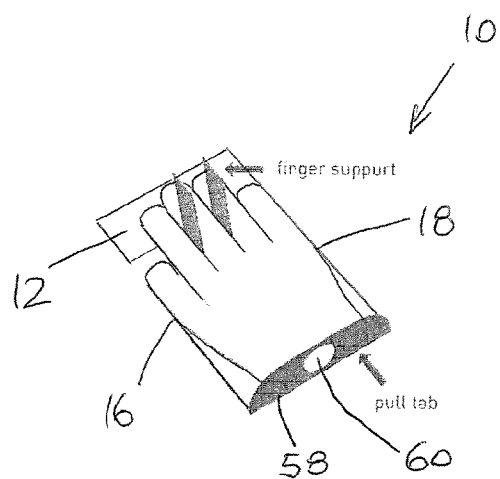
FIG. 5 shows a perspective view of a cartridge in accordance with a further embodiment of the present disclosure, with a disposable glove located at the cartridge.
Figure 6:
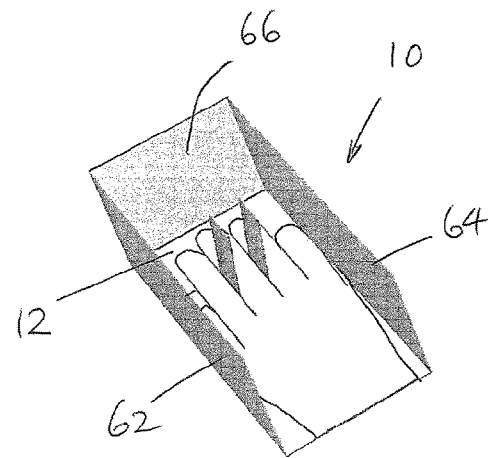
FIG. 6 shows a perspective view of a cartridge in accordance with a further embodiment of the present disclosure, with a disposable glove located at the cartridge.

When in use to support one or more disposable gloves 14 at the cartridge 10, each of the strips 24, 26 are located in use between any two adjacent fingers of the respective glove(s) 14. In the embodiment shown in FIG. 1, the strips 24, 26 are folded upward from the panel 12, and are respectively located between the thumb 32 and forefinger 34, and between the ring finger 36 and pinkie finger 38 of the glove(s) 14 (that is, the outermost pair of a user's fingers). In the embodiment shown in FIGS. 3, 5 and 7, the strips 24, 26 are folded upward from the panel 12, and are respectively located between the forefinger 34 and middle finger 42, and between the middle finger 42 and the ring finger 36 of the glove(s) 14, being two different adjacent fingers of the respective glove(s) 14. These glove alignment support strips 24, 26 facilitate better stacking of the gloves and thus easier mechanised removal of the gloves 14, one by one, from the stack, as will be described.

Figure 3:
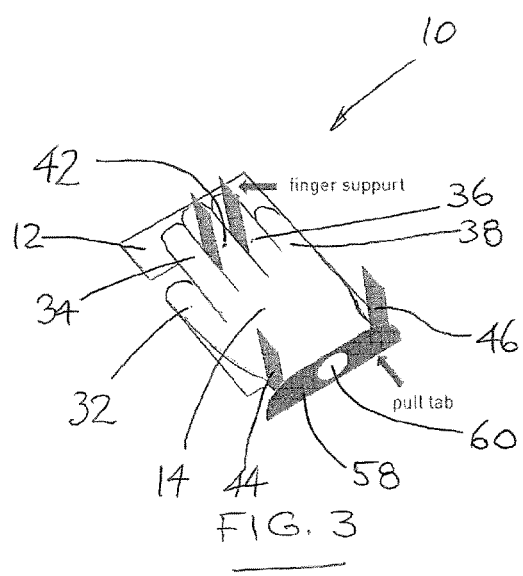
FIG. 3 shows a perspective view of a cartridge in accordance with a further embodiment of the present disclosure, with a disposable glove located at the cartridge.
Figure 4:
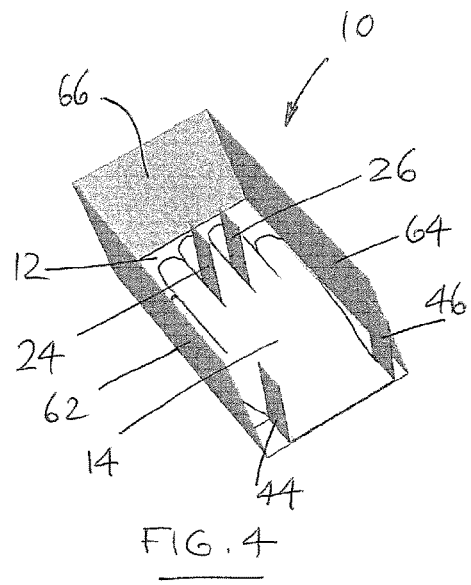
FIG. 4 shows a perspective view of a cartridge in accordance with a further embodiment of the present disclosure, with a disposable glove located at the cartridge.

In FIG. 3, the cartridge 10 also includes two additional rectangular strip portions 44, 46 of the panel 12 which are partially separable from the body of the remainder of the panel 12 along two parallel, frangible score lines, so as to each be able to be folded in a hinged manner into an upwardly oriented strip 44, 46, and to lie transverse of the cartridge panel 12. Both strips 44, 46 remain joined to the cartridge panel 12 at the hinge line, and detachment from the panel does not occur in normal use. As shown in FIG. 3, the strips 44, 46 have parallel sides, for ease of detachment from the remainder of the panel 12. The strips 44, 46 are located on either side of the open end (or cuff, or wrist region) 22 of the respective glove(s) 14, so that the glove(s) 14 are supported and more easily stacked therebetween. The additional support provided by the strips 44, 46 located on either side of the open end 22 of the glove(s) 14, along with the alignment support of the two strips 24, 26 located between two adjacent fingers of the gloves 14, means that the disposable gloves 14 can be stacked more neatly on the cartridge 10, and therefore dispensed from the cartridge 10 with fewer problems, as will be explained hereinafter.

Figure 7:
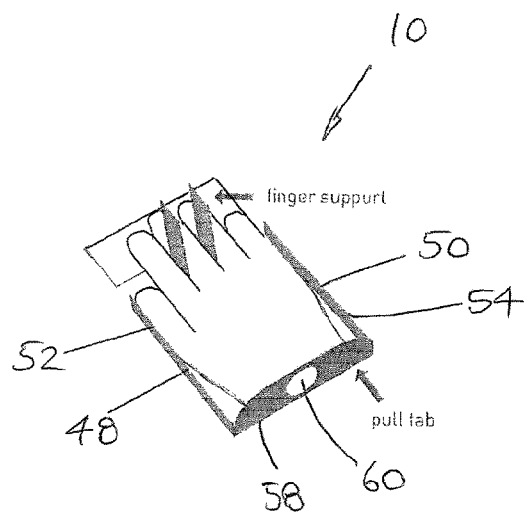
FIG. 7 shows a perspective view of a cartridge in accordance with a further embodiment of the present disclosure, with a disposable glove located at the cartridge.
Figure 8:
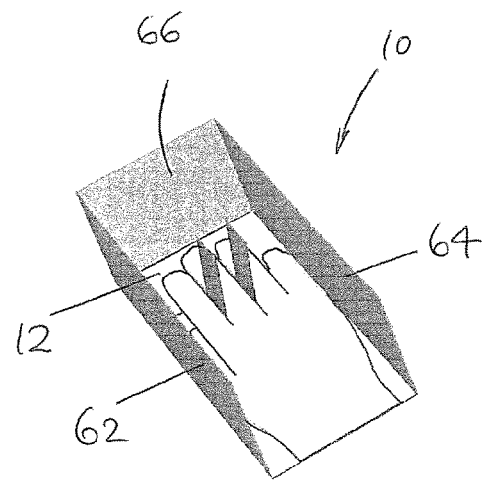
FIG. 8 shows a perspective view of a cartridge in accordance with a further embodiment of the present disclosure, with a disposable glove located at the cartridge.

In FIG. 7, the cartridge 10 also includes two additional rectangular strip portions 48, 50 of the panel 12 which are located on the left 52 and right 54 sides of the cartridge panel 12 along two parallel, fold lines, so as to each be able to be folded in a hinged manner into an upwardly oriented side strip 48, 50, and to lie transverse of the cartridge panel 12. Both strips 48, 50 remain joined to the cartridge panel 12 at the hinge line, and detachment from the panel 12 does not occur in normal use. As shown in FIG. 7, the strips 48, 50 are located on either side 52, 54 of the panel 12 and spaced apart by the width of a glove 14 laid flat (a width from the thumb side 16 to the pinkie finger side 18). These strips 48, 50 are folded upward with respect to the panel 12, and are respectively located adjacent the thumb side 16 and on the pinkie finger side 18 of the glove(s) 14. In the embodiment shown in FIG. 7, the side strips 48, 50 are used for alignment of the glove(s) 14 in combination with the alignment support provided by the two strips 24, 26 located between two adjacent fingers of the gloves 14, so as to promote neat stacking. These side strips 24, 26 can also facilitate the sliding motion of the cartridge 10 into a closure in the form of a box 56.

In alternatives to any of the preceding or foregoing embodiments described herein, the use of a single rectangular strip portion (such as shown by either part number 24 or 26 in the Figures) for alignment between just two adjacent fingers is also possible. Such a single strip can be partially separable from the body of the remainder of the panel along two parallel, frangible score lines, so as to be able to be folded in a hinged manner into an upwardly oriented strip, and to lie transverse of the base panel 12 of the cartridge. The inventors have shown that even the use of a single element such as a single strip between any two adjacent fingers can be sufficient to promote neat stacking of the gloves 14 without any other strip or flap or other element needed for in use alignment of a plurality of gloves located at the cartridge. Also in further alternatives of this, the use of a single finger divider strip between any two adjacent fingers does not need to be in the form of a portion of the base panel 12 which is partially detached therefrom and hingedly deployed upward, but can be a standalone protrusion or projection which is otherwise formed pre-attached or pre-affixed to sit proud of the supporting base panel of the cartridge prior to use, for example by gluing.

In still further alternatives to any of the preceding or foregoing embodiments described herein, the cartridge may have the option of using just a single strip portion 44 or 46 (being either partially separable from the body of the remainder of the panel 12 along two parallel, frangible score lines, or attached to the cartridge base panel by some other means of affixing to sit proud thereof), and located at the cartridge base panel 12 on one side of the open end 22 (or cuff, or wrist region) of the glove(s), so that the glove(s) 14 are sufficiently supported. The inventors have shown that even the use of a single element such as a single strip near the open end 22 (or cuff region) of the glove(s) can be sufficient to promote neat stacking of the gloves 14 without any other strip or flap or other element needed.

In still further embodiments, a strip or flap or other shaped element for in use alignment of a plurality of gloves located at the cartridge does not need to be in the form of a projection from, or a part of, the base panel 12 but can be a standalone protrusion or projection which extends inwardly towards the location of the glove(s) in use, for example from a side wall of the cartridge if there is one present. For example, there are cartridge side walls 62, 64 which are shown in FIGS. 2, 4, 6 and 8 in which in certain embodiments of the cartridge 10 the base panel 12 and the cartridge side walls 62, 64 as well as the end wall 66 can be integrally formed. Therefore, from these side walls, various shapes of strip portions or flaps can be at least partially detached or folded to extend into the interior space of the cartridge 10, and be used to support some part of the glove(s), such as between the fingers, or to align the open end 22 (or cuff region).

In a further example, the cartridge side wall interiors (for example those shown in FIGS. 2, 4, 6 and 8 as parts 62, 64) may have protrusions or formations thereon of various internal shape elements, such as curves, contours or other shapes which are arranged to extend into the interior space of the cartridge 10, and for example be used to closely abut and support either one or both of the left side edge or right side edge of each glove when the glove is oriented flat (laid parallel to the base panel 12 of the cartridge). Depending on the nature and style of gloves which are ultimately going to be stacked into the cartridge, the features of these protruding elements or formations may be changed during manufacturing of the cartridges to be of any other suitable shape or form which can closely accommodate the external dimensions of the glove, and so to facilitate even, aligned stacking of a plurality thereof.

In some of the preceding embodiments, a pull-tab flap 58 located on an end of the cartridge base panel 12 can facilitate the sliding motion of the cartridge 10 into or out of a closure or box 56, the pull tab 58 also having a finger hole grip 60. This pull-tab flap 58 means that the hands of an operator who is packing boxes 56 does not come into contact with the stacked, aligned gloves 14 on the cartridge 10.

Each of FIGS. 2, 4, 6 and 8 depict embodiments of the respective cartridge designs of FIGS. 1, 3, 5 and 7, with the additional feature of the cartridge 10 being either slidingly received into a respective closure or box 56, or integrally formed and itself being the base panel 12 of the box 56. In these example Figures, each box 56 comprises two parallel side walls 62, 64, a base panel 12 and an end wall 66, where the base 12 and the end wall 66 each extend between the two side walls 62, 64. The base panel 12 of the box 56 is of a cross-sectional shape equivalent to the shape dimensions of a respective cartridge 10, so that in inserted cartridge type arrangements, the cartridge 10 can be slidingly inserted into the end of the box 56 and locatable over the base panel 12 of the box 56. The side walls 62, 64 of the box 56 are of a height equivalent to (or more than) the height of the upwardly oriented, hinged strips 24, 26, when deployed transverse of the cartridge panel 12. The side 62, 64 and end 66 walls of the box 56 provide support for, and sterile containment of, the stacked and aligned gloves 14 on the cartridge 10, and are suitable for use into a glove dispensing machine, as will be shortly described. In some embodiments, the closure is a lidded box, as will be described in relation to FIG. 9.

Figure 9:
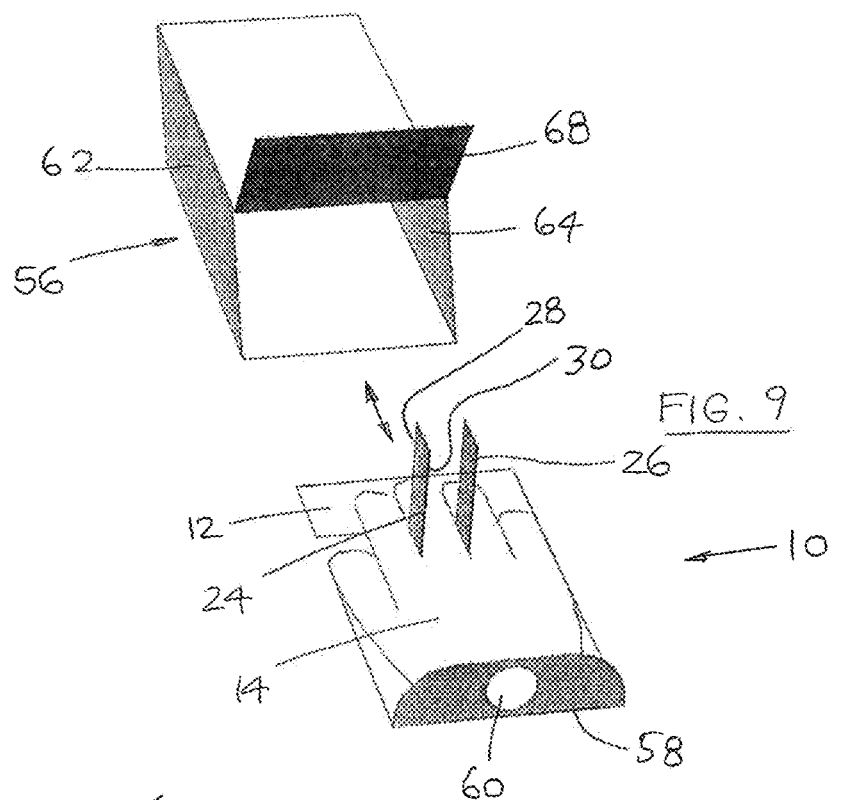
FIG. 9 shows a perspective view of the cartridge and glove of FIG. 5, along with a closure in the form of a lidded box into which the cartridge and glove(s) are slidingly locatable.

As shown in FIG. 9, the cartridges 10 are slidingly located into a box 56 with an openable end flap 68. In such inserted cartridge arrangements, the cartridge 10 can be slidingly removed from the box 56 in situations which necessitate the gloves 14 being removed from their box for dispensing, whereas integrated cartridges are intended to be built directly as part of a box with dispensing of gloves 14 to be undertaken directly from the opened box. In the arrangement shown in FIG. 9, in use the box end flap 68 is openable to allow the glove cartridge 10 which is inserted into the box 56 after being loaded with stacked, aligned gloves 14, to be slidingly removed to provide access to the gloves 14 by a dispenser machine. The sequence of drawings shown in FIGS. 10(*a*) to 10(*c*) respectively show the gloves 14 being stacked onto the cartridge 10 with finger support strips 24, 26 (FIG. 10(*a*)), then packed into the box 56 by using the box sides 52, 54 as a support for alignment of the side edges 16, 18 of the stacked, aligned gloves 14 so as to promote neat stacking, and also to guide to slide the cartridge base panel 12 in via an end of the box 56, using the pull tab flap 58 to push the cartridge 10 into the box 56 (FIG. 10(*b*)). The box end flap 68 is then closed and sealed with a closure clip or perhaps with an adhesive glue at its outer edges (FIG. 10(*c*)) to prevent access to the gloves 14.

Figure 10A:
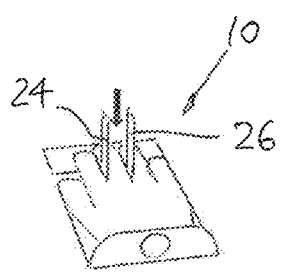
FIGS. 10(a), 10(b) and 10(c) show a consecutive sequence sequence of how the cartridge and glove of FIG. 9 is slidingly received into the lidded box of FIG. 9, and how the box lid is able to be closed.
Figure 10B:
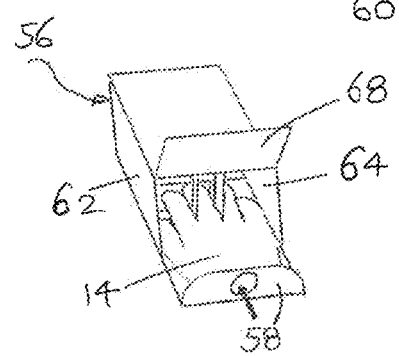
Figure 10C:
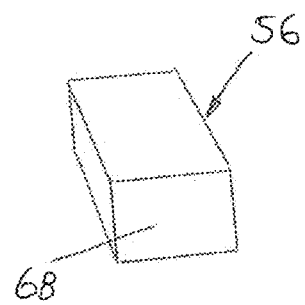
Figure 10D:
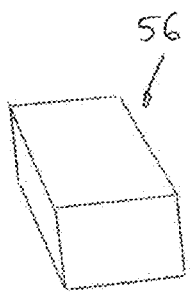
FIGS. 10(d), 10(e) and 10(f) show a consecutive sequence of how the cartridge and glove of FIG. 9 is slidingly removed from the lidded box of FIG. 9 after the box lid is opened, to leave a free cartridge and gloves(s) for use.

The sequence of drawings shown in FIGS. 10(*d*) to 10(*f*) respectively show the reverse sequence of the packed glove cartridge 10 being removed from the sealed box 56 (FIG. 10(d)). The box 56 is opened by releasing clips at the front end or by tearing along perforated edges or breaking an adhesive seal. A user then grabs the pull tab flap 58 to slidingly pull the loaded cartridge 10 out of the box 56 (FIG. 10(e)). Once removed from the box 56, the loaded cartridge 10 is now ready for the gloves 14 to be dispensed horizontally or vertically from the cartridge 10 by a glove delivery machine (FIG. 10(f)).

Figure 10E:
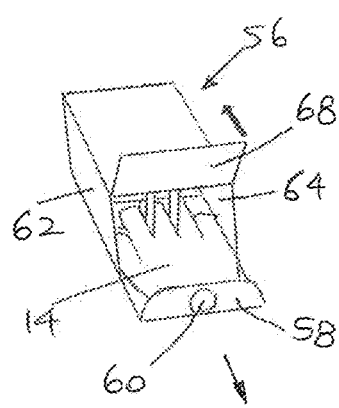
Figure 10F:
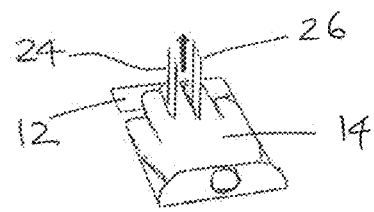

In a further embodiment of the methodology shown in FIGS. 10(d) to 10(f), the packed glove cartridge may not necessarily be removed from the sealed box (FIG. 10(d)). The box 56 can still be opened by releasing clips at the front end or by tearing along perforated edges or breaking an adhesive seal, and simply removing the upper lid 70. A user then would just place the unlidded box 56, including the loaded cartridge 10, into a dispensing machine for the gloves to subsequently be dispensed horizontally or vertically from the cartridge 10 by the glove delivery machine.

Figure 11:
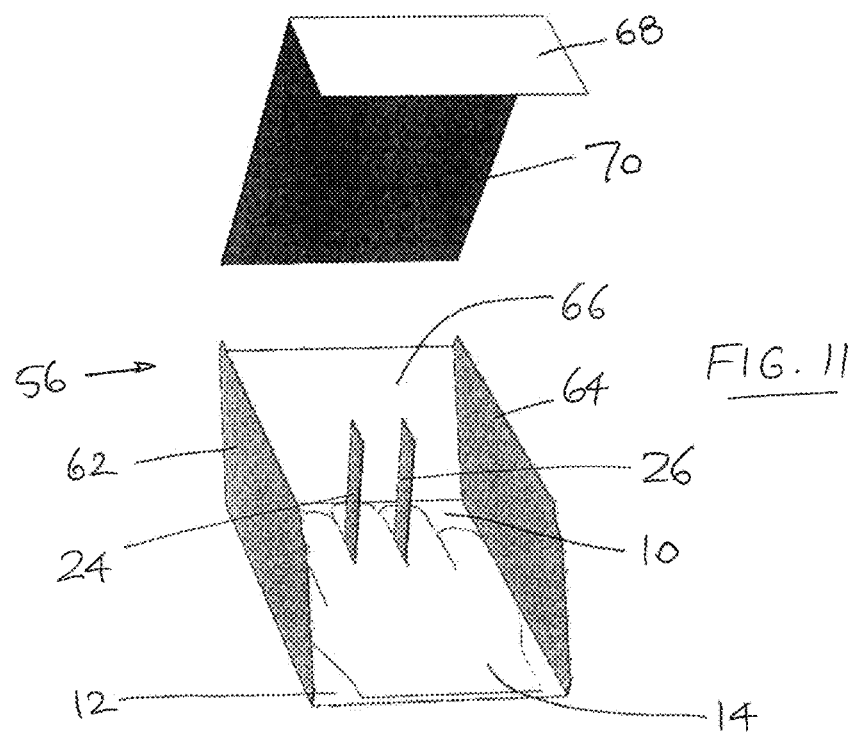
FIG. 11 shows a perspective view of the cartridge and glove of FIG. 6, where the cartridge is formed as an integrated part of a closure in the form of a lidded box for housing glove(s)
Figure 12A:
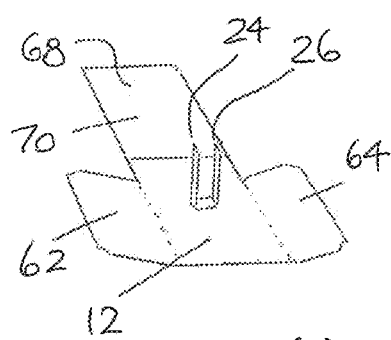
FIGS. 12(a), 12(b) and 12(c) show a consecutive sequence of how the integrated cartridge of FIG. 11 receives the glove(s) and then the closure in the form of a lidded box is assembled by folding for housing the glove(s).
Figure 12B:
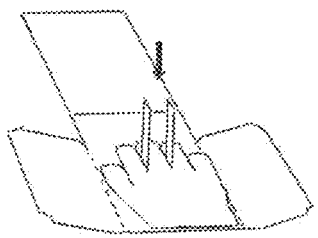
Figure 12C:
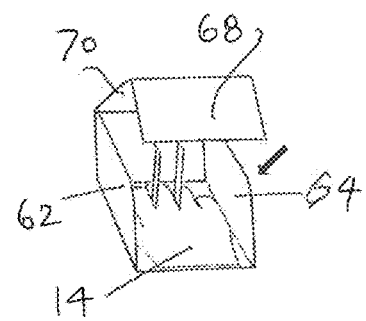

As shown in FIG. 11, the cartridges are formed as part of a box, which is openable with a tear-off top lid or lid and front flap combination. In such an integrated cartridge arrangement, the cartridge 10 is actually the base panel of the box 56, and dispensing is undertaken directly from the opened box 56. In the arrangement shown in FIG. 11, in use the box lid 70 and end flap 68 is torn off by a user to allow access by a dispenser machine to the stacked, aligned gloves 14 which lie within the remaining three walls 62, 64, 66 of the box 56. The sequence of drawings shown in FIGS. 12(a) to 12(c) respectively show the empty, unfolded box laid flat in preparation for filling with gloves to be stacked onto the cartridge 10 formed integrally as the base panel 12 of the box 56. Two finger support strips 24, 26 are joined to the cartridge base panel 12 of the box (FIG. 12(a)) for example by gluing, and then are bent or formed into a vertically upright position. Gloves 14 are then packed into the box by using the box sides 62, 64 and/or other raised support strips as a guide to proper alignment of the stacked gloves (FIG. 12(b)). It is better to stack the gloves vertically in this manner without the box walls 62, 64, 66 yet being formed around the finger support strips 24, 26, to allow ease of access and to prevent snagging or catching of the gloves on the side walls. Once the gloves 14 have been stacked, the box side walls 62, 64 and the lid 70 and end flap 68 are then folded up, closed and sealed with a closure clip, or perhaps with an adhesive glue at the outer edges (FIG. 12(c)). The box walls are at least of the height to accommodate the height of the deployed support strips 24, 26 when these are extended vertically from the cartridge base panel.

Figure 12D:
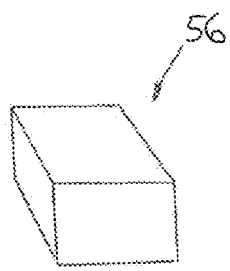
FIGS. 12(d), 12(e) and 12(f) show a consecutive sequence of how the lidded box of FIG. 11 containing the glove(s) is opened and the lid removed, to leave a free cartridge and glove(s) for use.
Figure 12E:
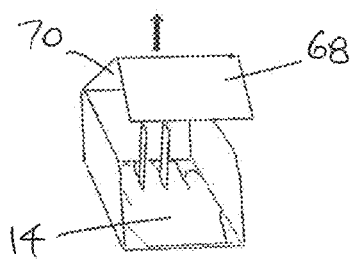
Figure 12F:
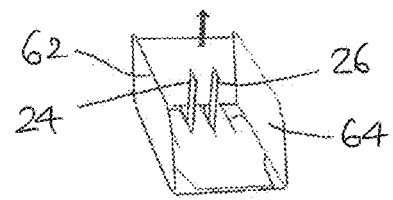

The sequence of drawings shown in FIGS. 12(d) to 12(f) respectively show the reverse sequence of the packed glove cartridge (being the base panel of the box) being exposed by the opening of the sealed box (FIG. 12(d)). The box 56 is opened by releasing clips at the front end flap 68 or by tearing along its perforated edges or breaking an adhesive seal, for example. A user then tears off the box lid 70 thereby exposing the stack of aligned gloves 14 seated in the remaining walls of the box (FIG. 12(e)). Once the lid has been removed or torn off from the box, the gloves are now ready to be dispensed vertically from the box by a glove delivery machine (FIG. 12(f)) without the necessity to slidingly remove a base cartridge, as was described earlier in relation to the embodiment shown in FIGS. 9 and 10.

Figure 13:
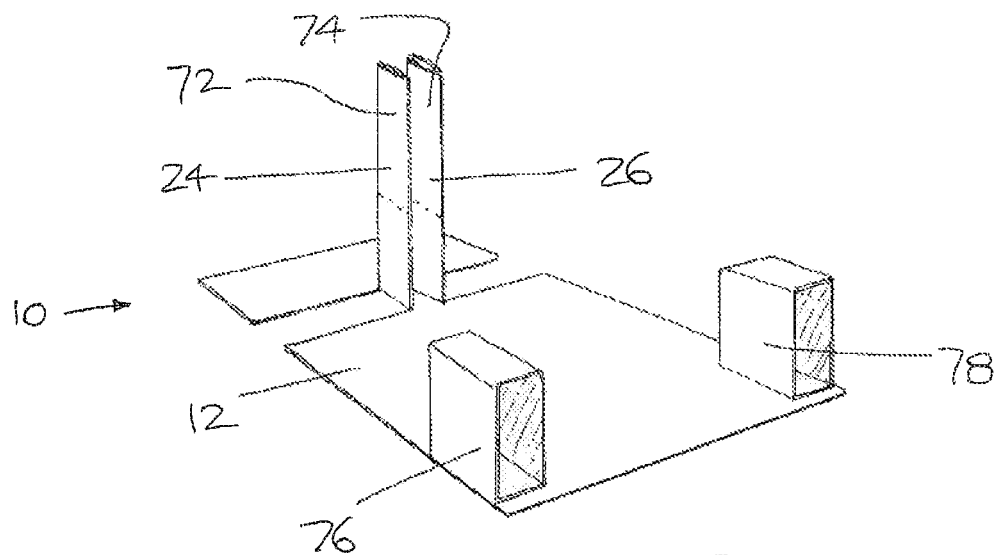
FIG. 13 shows a perspective view of a cartridge in accordance with a further embodiment of the present disclosure.

Turning to FIGS. 13 and 14, an insert cartridge 10 of the type already described is shown featuring two strips 24, 26 folded upward and extending from the base panel 12 for location between two adjacent fingers of the glove(s) 14 when stacked. In the embodiment shown in FIG. 13, the strips are arranged for location between the between the forefinger 34 and middle finger 42, and between the middle finger 42 and the ring finger 36 of the glove(s), being two different adjacent fingers of the respective glove(s). These glove alignment support strips 24, 26 can also have a removable, additional height extension sleeve 72, 74 each fitted thereto, as required.

Figures 14A, 14B:
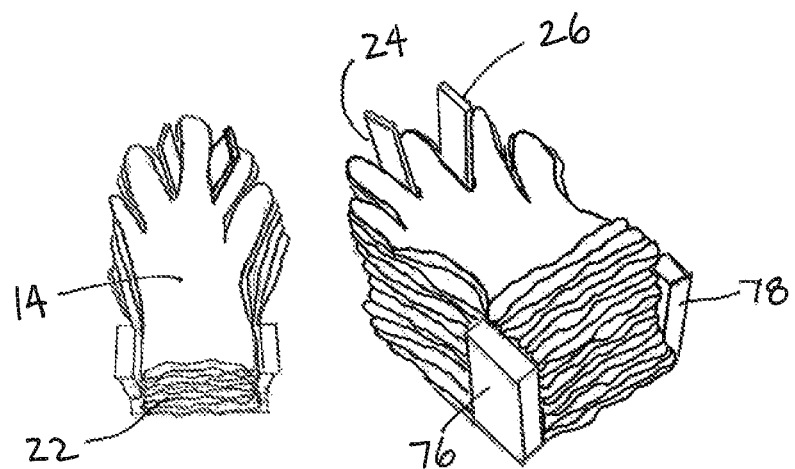
FIG. 14(a) shows a plan view of the cartridge of FIG. 13, with a stack of disposable gloves located at the cartridge.
FIG. 14(b) shows a perspective view of the cartridge of FIG. 13, with a stack of disposable gloves located at the cartridge.

In FIG. 13, the cartridge 10 also includes two additional box-shaped portions 76, 78 attached to the panel 12 by gluing, or by some other attachment means. These box-shaped portions 76, 78 could also be formed from a strip of material extending from the cartridge panel 12, and folded in a hinged manner into the upwardly oriented box shape 76, 78, so as to protrude vertically from the cartridge panel 12. In use the box-shaped portions 76, 78 are located on either side of the open end 22 (or cuff, or wrist region) of the glove(s) 14, so that the glove(s) are supported and more easily stacked therebetween. The additional support provided by the box-shaped portions 76, 78 located on either side of the open end 22 of the glove(s), along with the alignment support of the two strips 24, 26 located between two adjacent fingers of the gloves 14, means that the gloves can be stacked more neatly on the cartridge 10, and therefore dispensed from the cartridge with fewer problems. FIGS. 14(a) and 14(b) show two views of the stack of disposable gloves 14 when located at the cartridge 10 of FIG. 13. It has been found that the stack of aligned gloves 14 is better dispensed by a machine when the open end 22 (or cuff, or wrist region) of the gloves 14 are properly aligned, and this may have more influence on effective machine operation than the finger support provided by the two strips 24, 26 which are folded upward and extend from the base panel 12 of the cartridge 10.

Referring now to FIGS. 15(a) and 15(b), the cartridge of FIG. 13 is shown being vertically loaded onto a mounting bracket 80 which has rigid side walls, and may be made of metal or plastic, for example. The use of such a mounting bracket 80 can further facilitate the alignment of the stacked gloves 14 when being loaded onto the cartridge 10.

Referring now to FIGS. 16(a) through 16(d), the cartridge of FIG. 13 is shown vertically loaded onto a mounting bracket 82 which has no side walls, but which has two support posts 84, 86 against which the two respective strips 24, 26 which are folded upward and which extend from the base panel 12 can rest against during the glove stacking and filling step. These support posts 84, 86 are rounded in cross-section, so as to prevent any possible damage to an adjacent plastic glove 14 in use, and provide addition support for the strips 24, 26 during the glove stacking process to reduce the flexibility of the strips 24, 26, which may become bent or sag sideways with use. If the cartridge strips 24, 26 are able to extend close to vertically from the cartridge base panel 12, it makes it easier to load the glove 14 and to get the fingers in line, so as to produce a vertical glove stack. As shown in the drawings, the mounting bracket 82 also keeps the box-shaped portions 76, 78 located on either side of the open end 22 (or cuff, or wrist region) of the glove(s) 14, in square alignment, which therefore aids in the evenness of stacking of the open end regions 22 of the gloves 14.

In still further embodiments, the cartridge may have either of: (a) two rectangular strip portions 24, 26 (being either partially separable from the body of the remainder of the panel 12 along two parallel, frangible score lines, or attached to the cartridge base panel by some means), with each strip 24, 26 located between two adjacent fingers of the glove(s)

14; or (b) two rectangular strip or box portions 48, 50 located at the cartridge base panel 12 on either side of the open end 22 (or cuff, or wrist region) of the glove(s), so that the glove(s) 14 are supported. It is possible for either of these two arrangements of glove support to solely facilitate the gloves being neatly stacked on the cartridge 10, and therefore dispensed from the cartridge 10 with fewer problems. In still further embodiments of these two types of arrangements, the cartridge 10 itself may form the base panel 12 of the box 56, with dispensing occurring directly from the opened box.

In still further embodiments, the cartridge may have either of: (i) one rectangular strip portion (24 or 26) (being either partially separable from the body of the remainder of the panel 12 along two parallel, frangible score lines, or attached to the cartridge base panel by some means), with the strip located between two adjacent fingers of the glove(s); or (ii) one rectangular strip or box portion (76 or 78) located at the cartridge base panel 12 on one side of the open end 22 (or cuff, or wrist region) of the glove(s), so that the glove(s) are supported. It is possible for either of these two arrangements of glove support means to solely facilitate the gloves 14 being neatly stacked on the cartridge 10, and therefore dispensed from the cartridge 10 with fewer problems. In still further embodiments of these two types of arrangements, the cartridge 10 itself may form the base panel 12 of the box 56, with dispensing occurring directly from the opened box.

Figure 17A:
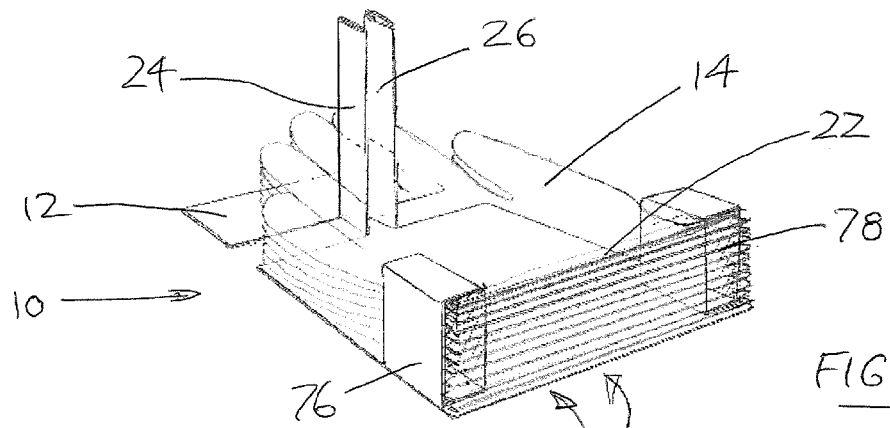
FIG. 17(a) shows a perspective view of the cartridge of FIG. 13, with a stack of disposable gloves located at the cartridge; the open end of each disposable glove being fitted with a planar element which is supported by the cartridge in use.
Figure 17B:
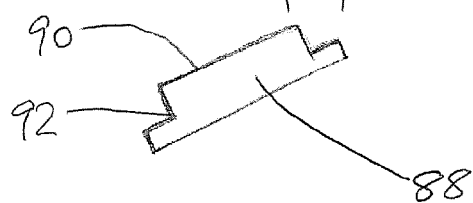
FIG. 17(b) shows a plan view of a planar element of FIG. 17(a)

Referring now to FIGS. 17(a) and 17(b), the cartridge 10 of FIG. 13 is shown being loaded with a plurality of adjacent, aligned, disposable gloves 14, where each one of the gloves has a generally rectangular-shaped planar tab 88 which is interfitted into the respective open end of each glove 14. These planar tabs 88 each have a tongue portion 90 which extends at least partially into the open end 22 of each glove 14, and held there by the elasticity of the glove material. The tabs 88 which are fitted into each glove 14 also have a shoulder section 92 which in use rests against the outer edge of the two box-shaped portions 76, 78 of the cartridge 10. By this method, each glove 14 is supported in an aligned manner by positioning the shoulder section 92 of the tab 88 to rest against the box-shaped portions 76, 78 of the cartridge 10. If necessary, the gloves 14 can still be further supported by either one or two rectangular strip portions 24, 26 (being either partially separable from the body of the remainder of the panel 12 along two parallel, frangible score lines; or, attached to the cartridge base panel 12 by some means), with the or each strip 24, 26 located between any two adjacent fingers of the glove(s), as described in previous embodiments.

Figure 18A:
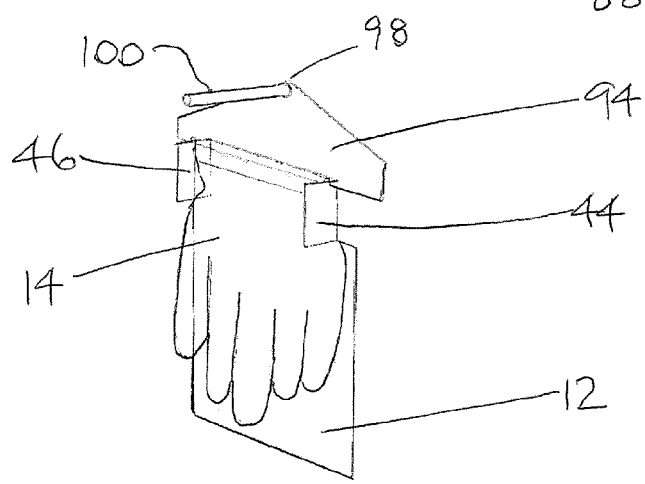
FIG. 18(a) shows a perspective view of the cartridge of FIG. 13, with one disposable glove located at the cartridge, the open end of the disposable glove being fitted with a planar element which is supported by the cartridge in use.
Figure 18B:
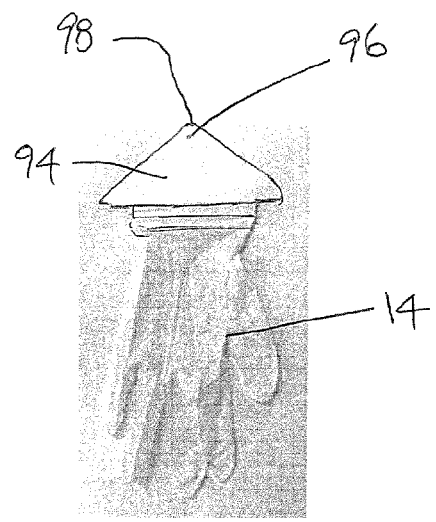
FIG. 18(b) shows a plan view of a disposable glove, the open end of the disposable glove being fitted with the planar element of FIG. 18(a)

Referring now to FIGS. 18(a) and 18(b), the adjacent, aligned, disposable gloves, each have a generally triangular-shaped planar tab 94 which is interfitted into the respective open end 22 of each glove 14. These planar tabs 94 function in the same way as the rectangular tabs 88 with shoulder 92 as described in FIGS. 17(a) and 17(b), but each tab 94 also has a through-hole 96 located near the apex 98 of the planar tab 94, meaning that the tabs 94 and attached gloves 14 can be aligned on a rod 100 or wire, or similar elongate member. In some dispensing arrangements it may be convenient for the gloves to be vertically, adjacently aligned and then packed, as shown in the orientation shown in FIG. 18(a). Also as shown in FIG. 18(a), there is a cartridge 10 into which the tabs 94 and attached gloves 14 can be aligned and positioned, and the cartridge 10 also has two rectangular strip portions 44, 46 located at the cartridge base panel 12 on either side of the open end 22 (or cuff, or wrist region) of the glove(s) 14, in square alignment with one another, which therefore aids in the evenness of stacking of the open end 22 region of the gloves 14. This improved stacking assists with the procedure of dispensing the gloves 14 from the cartridge 10.

Figure 19:
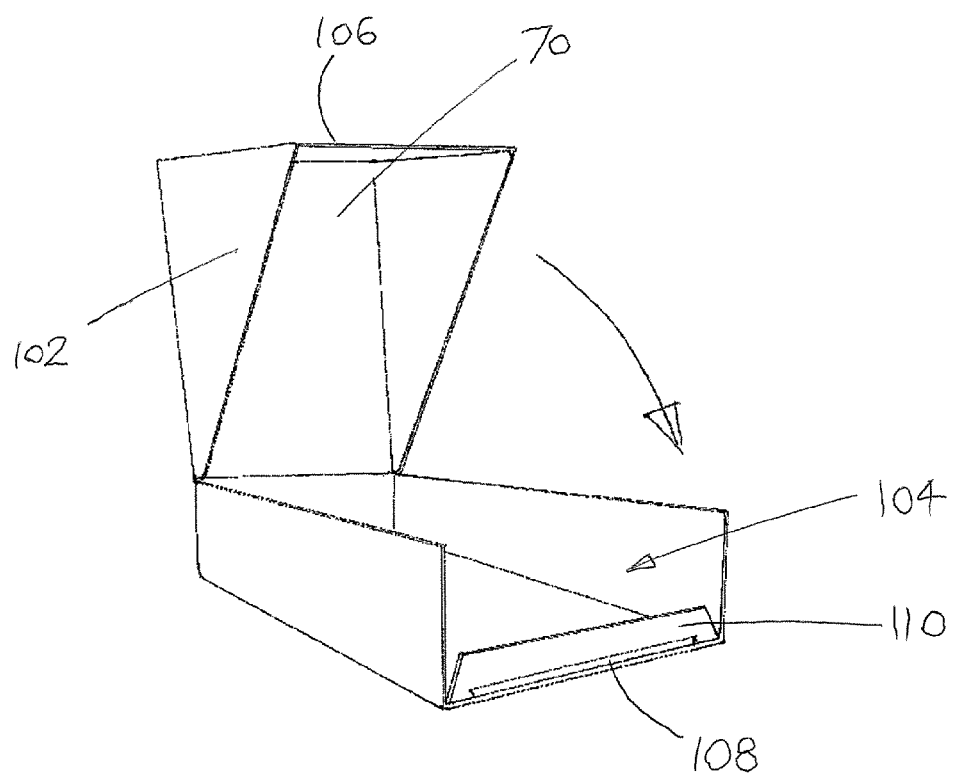
FIG. 19 shows a perspective view of an embodiment of a lidded box for sliding receipt of a cartridge in accordance with the present disclosure, the lid of the box having side panels, and the lid being able to be interlockingly engaged in a closed position in use.

Once the gloves are positioned in an adjacent, aligned manner as shown in FIGS. 17(a) and 18(a), and the gloves 14 are supported on a cartridge 10 or at the base panel of a box, the planar tabs 88, 94 can be removed from the open end 22 of each of the gloves 14 in the stack of gloves. The stacked, adjacent gloves are then placed in some sort of closure or box 56, either by sliding the cartridge 10 into the box 56, or forming the box 56 around the base panel 12 onto which the gloves 14 are stacked, and sealing the box 56, so that the gloves 14 are then ready to be dispensed by a glove delivery machine, as has been previously described for other embodiments. A further example of a closure of the type used to contain a cartridge of gloves is shown in FIG. 19, which includes triangular side panels 102 on the lid 70 which can increase the rigidity of the overall box 104 with the lid 70 closed. To effect closing engagement, the end edge 106 of the lid 70 is received in use into a slot 108 in a tab flap 110 formed at the edge of the base panel 12 of the box 104.

The present disclosure also relates to the features of a machine for dispensing disposable gloves for use on a user's hands, and methods for using such machines. In the embodiments disclosed, the gloves are stacked in an aligned, stacked manner in the cartridge, or in a box which contains, or includes, a cartridge, in accordance with any of the embodiments already described. The aim of any one of the illustrated dispensing machines is to automate the glove dispensing and opening processes, to be able to offer the glove to a user with minimal contamination of the external surfaces of the glove(s). In the following exemplary embodiments, if a component of both embodiments has the same or a similar functionality, it has been given the same part number for ease of reference.

Figure 20:
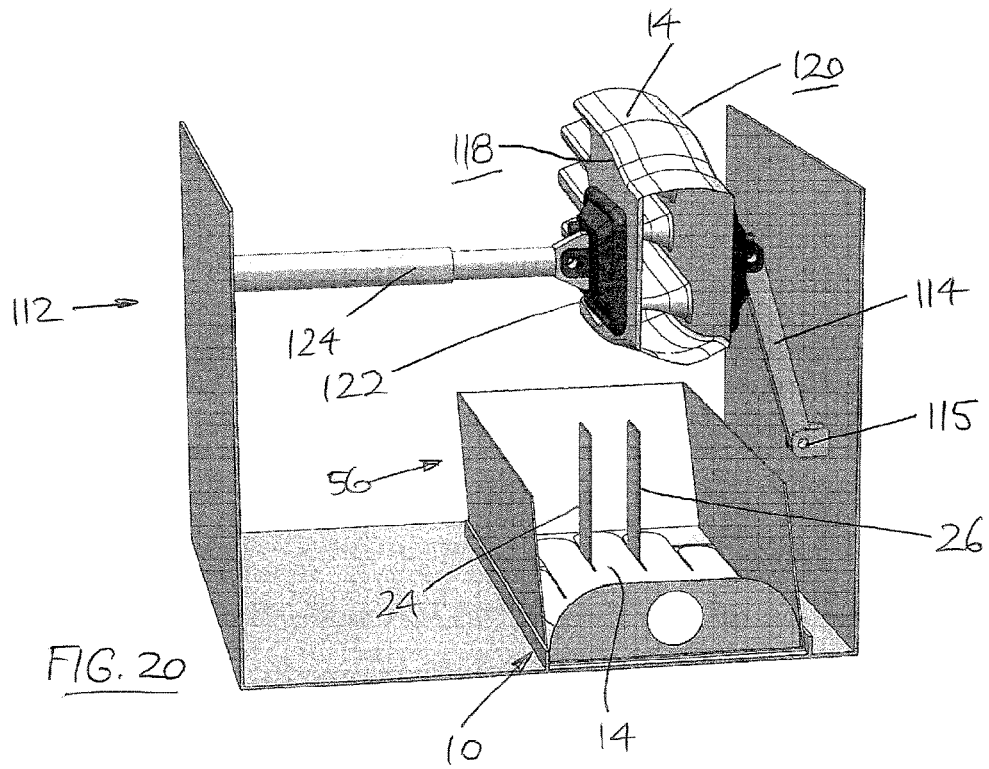
FIG. 20 shows a perspective, schematic view of an embodiment of a glove dispensing machine in accordance with the present disclosure, with a disposable glove shown in an open position.
Figure 21A:
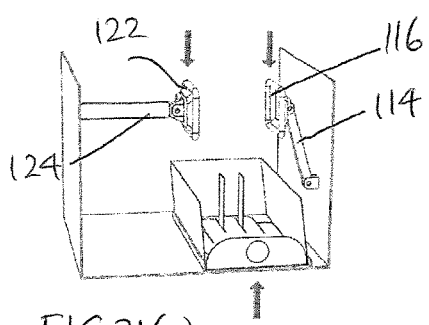
FIGS. 21(a), 21(b), 21(c), 21(d) and 21(e) show a sequence of steps of how the machine of FIG. 20 is able to select a disposable glove and to open that glove for the entry of a user's hand.
Figure 21B:
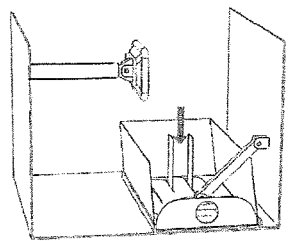
Figure 21C:
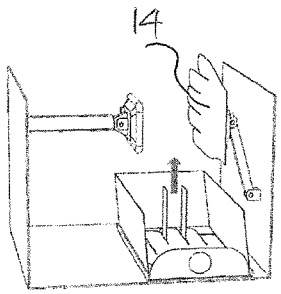
Figure 21D:
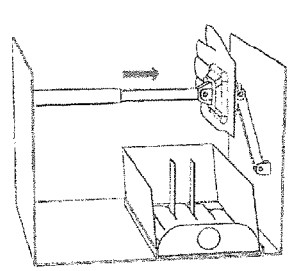
Figure 21E:
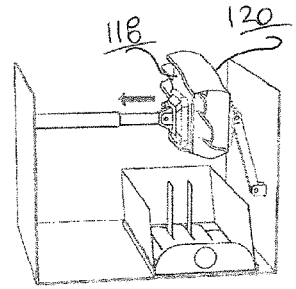

Referring now to the embodiment shown in FIG. 20, and in FIGS. 21(a) to 21(e), a dispensing machine 112 is shown in which a horizontal stack of gloves 14 is located in an open box 56 including a cartridge 10. The gloves 14 can be dispensed, one at a time, by the machine 112 which offers the glove to the user's hand in a vertical (or 'thumbs up') orientation without movement of the cartridge 10 from its initial position within the machine 112. The machine shown (FIG. 21(a)) has an articulated arm 114 which is fitted with a suction device in the form of a first suction cup 116, which has a square shaped front face. The articulated arm 114 is arranged in use to move the first suction cup 116 into a position to contact the glove 14, and then the suction cup 116 is actuated (that is, a suction pressure is applied) to retain one face (palmar side 118 or dorsal side 120) of a single glove by the application of the suction, as shown in FIG. 21(b). Actuation of the first suction cup 116 to retain the glove 14 then allows the retained glove to be moved by the action of the articulated arm 114 as the arm 114 pivots about a mounting point 115 which is located at an interior side wall of the dispensing machine 112 above the height of the cartridge 10. The glove 14 is lifted out from the cartridge or box 56 of horizontally stacked gloves, and is raised into a position above the cartridge 10 and, as shown in FIG. 21(c), because of the fixed angle between the front plane of first suction cup 166 and the axis of the articulated arm 114, the glove is now oriented orthogonally with respect to its original horizontal position. In such a vertical (or "thumbs up") orientation, as shown in FIG. 21(c). Actuation of suction can be as a result of activation of a suction pump.

The suction cup 116 has an exterior surface made of rubber, vinyl, pvc or some other flexible or plastic material, with rounded edges to ensure that there is no damage or tearing of the contacted glove in use.

Once the glove 14 is held in the aforementioned vertical orientation, an anchoring means in the form of a second suction cup 122, which is supported by being attached to an end of a telescopically moveable arm 124, which is laterally moveable in a direction across the top of the cartridge 10, so that the suction cup 122 can make contact with the other side of the glove 14 (the other one of the palmar side 118 or the dorsal side 120 which is not already attached to the first suction cup 116). The second suction cup 122 can then be actuated so as to retain the said other side of the glove by the application of suction. This means that the glove 14 is now held on both of its greater side faces 118, 120 by a respective suction cup 116, 122, and is therefore able to be stretched open if the moveable arm 124, is moved laterally in a reverse direction across the top of the cartridge 10 so that the second suction cup 122 is moved in a direction away from the respective other suction cup 116. In the embodiment shown in FIG. 21(e), the telescopically moveable arm 124 is retracted to move away from the stationary articulated arm 114, in use so as to stretch the glove 14 sufficiently wide at its open end 22 to enable admission of a human hand (this is also shown in a larger view in FIG. 20). The user can thus insert their hand into the open (cuff) end 22 of the glove 14 without the need to touch the exterior of the glove, and whilst the glove is presented in a 'thumbs up' orientation. Once the hand is inserted in the glove, the suction pressure being applied to both suction cups 116, 122 can be deactivated, allowing the release of the sides 118, 120 of the gloves from the suction cups 116, 122, so that a user can retract a gloved hand from the apparatus. The force of movement of the articulated arm 114 and of the telescopically movable arm 124 is never greater than the suction force pressure applied to either of the glove faces 118, 120, so as not to remove the glove 14 from either suction cup 116, 122 (which would not allow it to become opened for use), or to be so forceful as to tear the glove apart.

In other embodiments of the dispensing machine, the articulated arm holding the first suction cup may also have a telescopic functionality, and the second suction cup may be attached to an articulated arm, for example. In other embodiments of the dispensing machine, the telescopically moveable arm can remain stationary and the articulated arm can retractably move in use relative to the telescopic arm, so as to stretch the glove sufficiently wide at its open end to enable the admission of a human hand. The use of suction cups has the advantage of no contact contamination with the outer surfaces of the glove, although in still further embodiments, the use of a suction cup can be replaced by use of another form of temporary bonding, such as adhesive or 'tacky' surface, which is sufficient to join to the face(s) of the glove in a non-permanent manner, but is still sterile.

Figure 22:
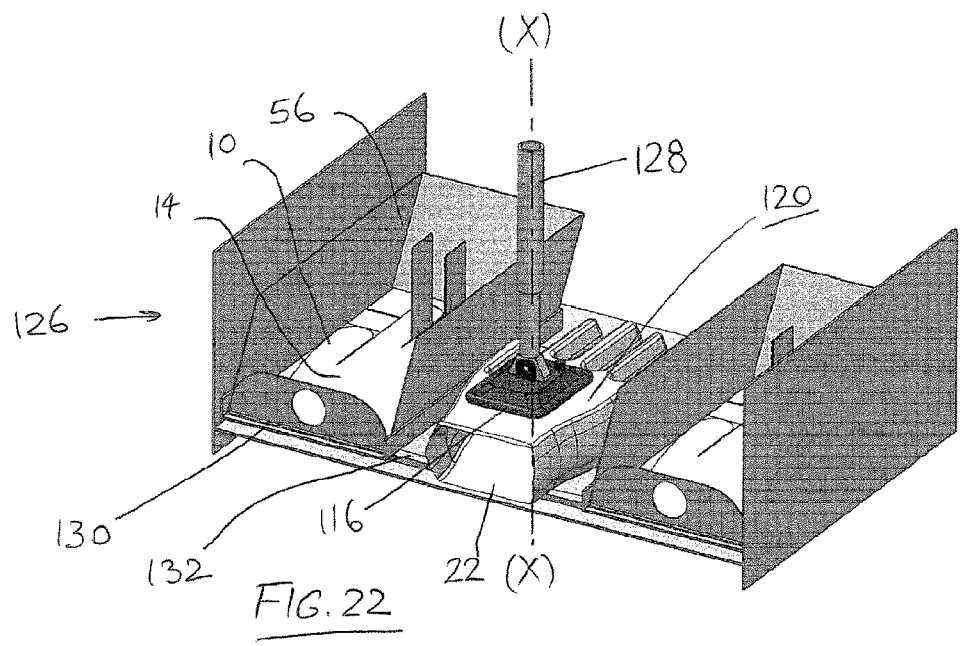
FIG. 22 shows a perspective, schematic view of a further embodiment of a glove dispensing machine in accordance with the present disclosure, with a disposable glove shown in an open position.
Figure 23A:
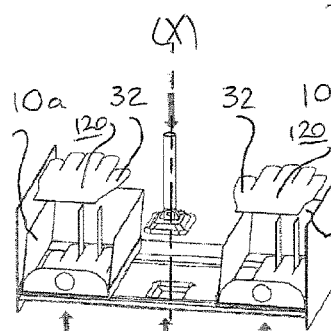
FIGS. 23(a), 23(b), 23(c), 23(d), 23(e), 23(f), 23(g) and 23(h) show a sequence of steps of how the machine of FIG. 22 is able to select a disposable glove and to open that glove for the entry of a user's hand.
Figure 23B:
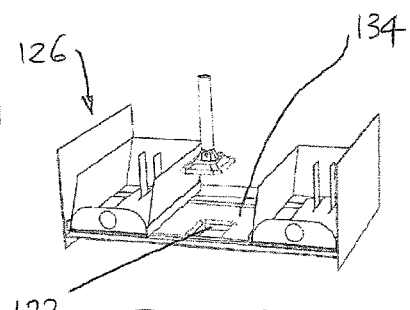
Figure 23C:
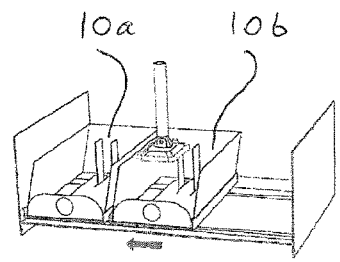
Figure 23D:
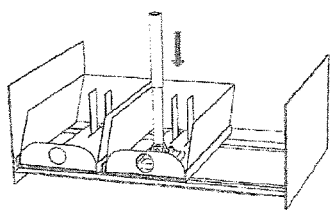
Figure 23E:
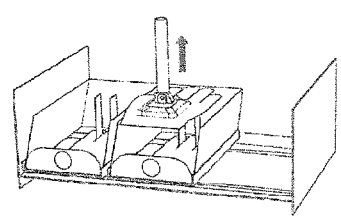

Referring now to the embodiment shown in FIG. 22, and in FIGS. 23(a) to 23(h), a dispensing machine 126 is shown in which a horizontal stack of gloves 14 in an open box 56 including a cartridge 10. The gloves can be dispensed, one at a time, by the machine 126 which offers the glove 14 to the user's hand in a horizontal (or 'thumbs sideways') orientation after movement of the cartridge 10 occurs. The machine 126 (FIG. 23(a)) has a single, centrally located, articulated arm 128 which operates using a telescopic extension and retraction mechanism. The lowermost end region of the articulated arm 128 is fitted with a first suction cup 116, of the type previously described in relation to FIG. 20 and FIG. 21. The telescopic arm 128 is arranged in use to move in a vertically direction upward or downward along the axis (X-X) of its length. The cartridge 10 (or box 56) of stacked gloves 14 is moveable by sliding laterally sideways with respect to the vertical axis X-X, and on a platform 130 located on a rail or track 132, and into a position so as to be aligned underneath the vertical axis X-X of the telescopic arm 128 (FIG. 23(c)). The telescopic arm 128 can then move the suction cup 116 downward into a position to contact a glove 14 at the cartridge 10 (FIG. 23(d)) and then be actuated so as to retain one face (palmar side or dorsal side 118, 120) of a single glove 14 by the application of air suction. The actuation of the first suction cup 116 to retain the glove 14 then allows the retained glove 14 to be moved by the action of the telescopic arm 128 out from the cartridge 10 (or box 56) of horizontally stacked gloves, and to be raised into a position above the cartridge 10, and held in the same horizontal orientation, as shown in FIG. 23(e)). The cartridge 10 is then moved laterally sideways from under the axis X-X of the telescopic arm 128 (FIG. 23(f)).

Figure 23F:
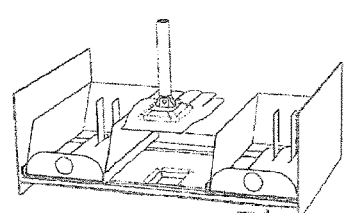
Figure 23G:
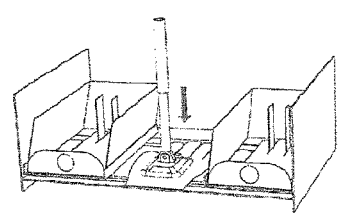
Figure 23H:
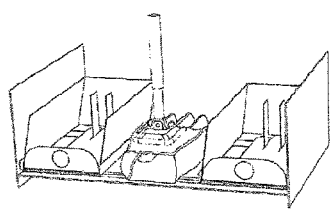

Once the cartridge 10 of undispensed gloves has been moved laterally sideways, a second, stationary suction cup 122 is exposed at the base or floor region 134 of the machine 126, below the rail or track 132 upon which the cartridge 10 (or box 56) of stacked gloves is laterally moved. The stationary suction cup 122 is positioned in alignment with the axis X-X of the telescopic articulated arm 128, as shown in FIG. 23(f). The glove 14 being held by the first suction cup 116 is then lowered in the vertically axial direction X-X towards the second suction cup 122, so that the second suction cup 122 can contact the other side face of the glove 14 (the other of the palmar side or dorsal side which is not already attached to the first suction cup 116). The second suction cup 122 can then be actuated by the application of suction so as to retain the said other side face of the glove 14. This means that the glove 14 is now held at both of its large side faces 118, 120 by a respective suction cup 116, 122, and is therefore able to be stretched open if the telescopic arm 128 is moved in an axial direction X-X vertically upward and away from the second, stationary suction cup 122. In the embodiment shown in FIG. 23(h), the telescopically moveable arm 128 moves away from the stationary suction cup 122, in use so as to stretch the glove cuff sufficiently wide at its open end 22 to enable admission of a human hand (this is also shown in a larger view in FIG. 22). The user can insert their hand into the open (cuff) end 22 of the glove 14 without the need to touch the exterior of the glove, and in a 'thumbs sideways' orientation (palm facing the ground, or palm facing upwards). Once the hand is inserted in the glove, the suction pressure being applied to both suction cups 116, 122 can be deactivated, allowing the release of the sides 118, 120 of the gloves 14 from the suction cups 116, 122, so that a user can retract the gloved hand from the apparatus. The force of movement of the telescopic arm 128 is never greater than the suction force pressure applied to either of the glove faces 118, 120, so as not to remove the glove 14 from either suction cup (which would not allow it to become opened for use), or to be so forceful as to tear the glove apart.

In the embodiment shown, there are two cartridges 10 of stacked, aligned disposable gloves 14 shown at the base or floor region 134 of the machine 126. In use, either of these cartridges 10 can be moved sideways by sliding along a track or rail 132 so as to be positioned under the vertical axis X-X of the telescopic arm 128, either alternately, or one at a time until the gloves 14 have all been dispensed from one cartridge 10 before switching to another cartridge/box 10. In the embodiment shown in FIG. 23(a), the gloves are stacked in a 'left hand' and a 'right hand' orientation—that is, the thumbs 32 of stacked gloves 14 in the left hand cartridge 10a are facing toward the axis X-X of the telescopic arm 128, with palms facing down, and the thumbs 32 of stacked gloves 14 in the right hand cartridge 10b are also facing toward the axis X-X of the telescopic arm 128, with palms facing down. This means that during use, the user could put both of their hands into the machine 126 one after another in sequence, in both cases in a 'palms down' orientation, offering either left hand first and then right hand, or vice versa, and a glove 14 would be dispensed from the respective left hand 10a and then, subsequently, from the right hand 10b cartridge, in the manner described above. The order of dispensing could also be reversed (that is, the right hand first and then the left hand, depending on the cartridge which is being accessed).

In another embodiment, the gloves may be stacked in the same direction in both cartridges—for example, all of the gloves in both cartridges could be oriented with the thumb on the left hand side of the cartridge and the pinkie finger on the right hand side of the cartridge. In such an arrangement, the user of the machine of FIG. 22 would need to alternate the orientation of their hands during insertion into the machine, with the user's right hand needing to be 'palms down' for receiving a glove from either of the cartridges, and the user's left hand needing to be oriented as 'palms up' for receiving a glove from either cartridge.

In other embodiments of the machine, the arm holding the first suction cup may also have an articulated functionality, and the second suction cap may be attached to a telescopic arm, for example.

Figure 24:
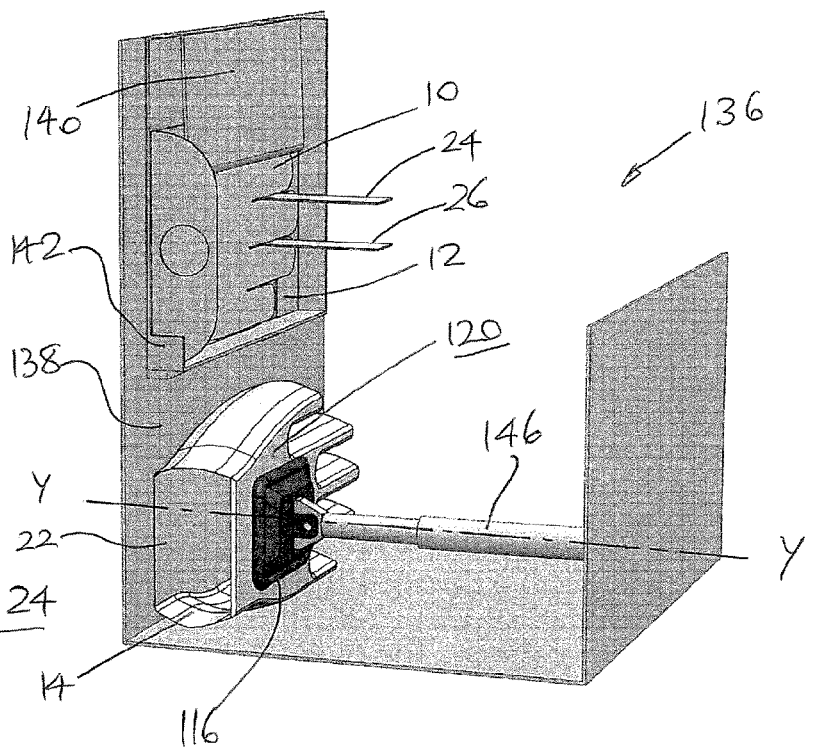
FIG. 24 shows a perspective, schematic view of a further embodiment of a glove dispensing machine in accordance with the present disclosure, with a disposable glove shown in an open position.

Referring now to the embodiment FIG. 24, and to FIGS. 25(a) to 25(f), a dispensing machine 136 is shown in which there is positioned a stack of gloves 14 in an open box 56 containing a cartridge 10 of such gloves, which has been oriented sideways in use in the machine 136. The stack of aligned gloves is held in position at an interior wall 138 of the machine 136 by means of a tension clip 140 which retains the stack of gloves 14 in an aligned manner so that they do not fall out of the cartridge 10 whilst in the sideways orientation. The cartridge 10 and the tension clip 140 are located together on a slidable platform 142 which can move vertically up and down along a rail 144 on the inside wall 138 of the machine 136, as will now be described. The gloves can be dispensed, one at a time, by the machine 136, which offers the glove 14 to the user's hand in a vertical (or 'thumbs up') orientation.

Figure 25A:
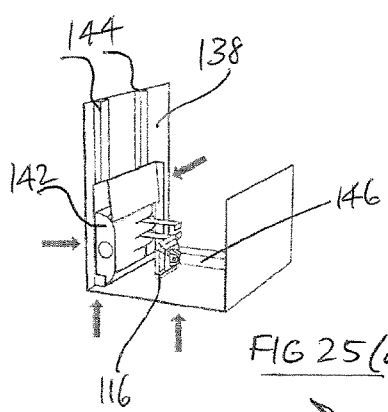
FIGS. 25(a), 25(b), 25(c), 25(d), 25(e) and 25(f) show a sequence of steps of how the machine of FIG. 24 is able to select a disposable glove and to open that glove for the entry of a user's hand.
Figure 25B:
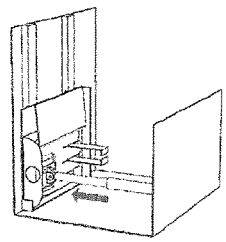
Figure 25C:
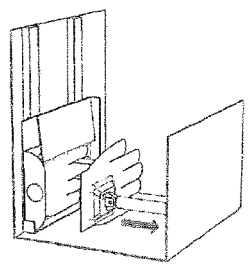

The machine shown (FIG. 24) has a single articulated arm 146 which operates using a telescopic extension and retraction mechanism. The terminal end region of the articulated arm 128 is fitted with a first suction cup 116 of the type previously described in relation to embodiments shown in FIG. 20 and FIG. 22. The telescopic arm 146 is arranged in use to move in a horizontally sideways direction along the axis (Y-Y) of its length. The cartridge 10 (or box 56) of stacked gloves 14 is oriented sideways and is moveable by sliding vertically up or down on a platform 142 located on a rail or track 144, and into a position so as to be aligned with the horizontal axis Y-Y of the telescopic arm 146 (FIG. 25(a)). The telescopic arm 146 can then move the suction cup 116 sideways into a position to contact a glove 14 at the cartridge 10 (FIG. 25(b)) and then be actuated so as to retain one face (palmar side or dorsal side) of a single glove 14 by the application of air suction. After actuation of the first suction cup 116 to retain the face of the glove 14, the telescopic arm 146 is then retracted to cause the retained glove 14 to be moved by the action of the telescopic arm 146 out from under the grip of the tension clip 140 and out of the cartridge 10 (or box 56) of stacked gloves. Once the glove 14 is moved into a position away from the cartridge 10, it is then held in a vertical orientation, as shown in FIG. 25(c)). The cartridge 10 and the tension clip 140 are then moved vertically upwards along the machine inner wall 138 by the action of the dispensing machine 136, and away from being in alignment with the horizontal axis Y-Y of the telescopic arm 146 (FIG. 25(d)).

Figure 25D:
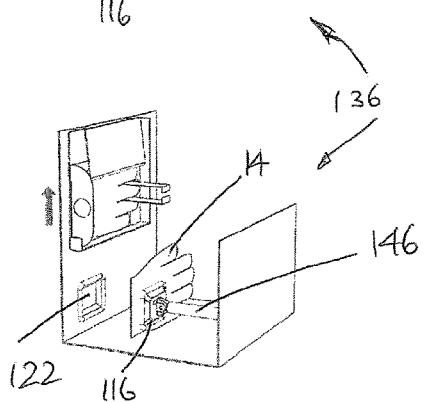
Figure 25E:
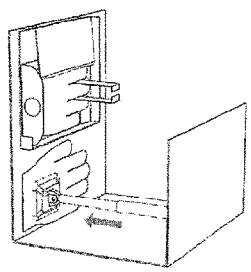
Figure 25F:
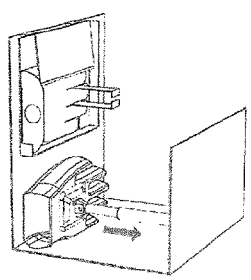

Once the cartridge 10 of undispensed gloves has been moved vertically upwards by sliding, the location of an anchoring means in the form of a second, stationary suction cup 122 is exposed at the wall 138 of the machine 136, and which is in alignment with the axis Y-Y of the telescopic arm 146, as shown in FIG. 25(d). The glove 14 being held by the first suction cup 116 is then moved sideways in the same horizontal axial direction Y-Y of the telescopic articulated arm 146 towards the second suction cup 122, so that the second suction cup 122 can contact the other side face of the glove (the other of the palmar side or dorsal side) as shown in FIG. 25(e). The second suction cup 122 can then be actuated so as to retain that other side face of the glove by the application of suction. This means that the glove 14 is now held on both of its greater side faces 118, 120 by a respective suction cup 116, 122, and is therefore able to be stretched open if the telescopic arm 146 is moved in an axial direction Y-Y horizontally away from the second suction cup 122. In the embodiment shown in FIG. 25(f), the telescopically moveable arm 146 moves away from the stationary suction cup 122, in use so as to stretch the glove sufficiently wide at its open end 22 to enable admission of a human hand (this is also shown in a larger view in FIG. 24). The user can insert their hand into the open (cuff) end 22 of the glove 14 without the need to touch the exterior of the glove 14, while the glove is presented in a 'thumbs up' orientation (palm facing sideways). Once the hand is inserted in the glove, the suction pressure being applied to both suction cups 116, 122 can be deactivated, allowing the release of the sides 118, 120 of the gloves 14 from the suction cups 116, 122, so that a user can retract the gloved hand from the apparatus. The force of movement of the telescopic arm 146 is never greater than the suction force pressure applied to either of the glove faces, so as not to remove the glove from either suction cup 116, 122 (which would not allow it to become opened for use), or to be so forceful as to tear the glove apart.

Figure 26:
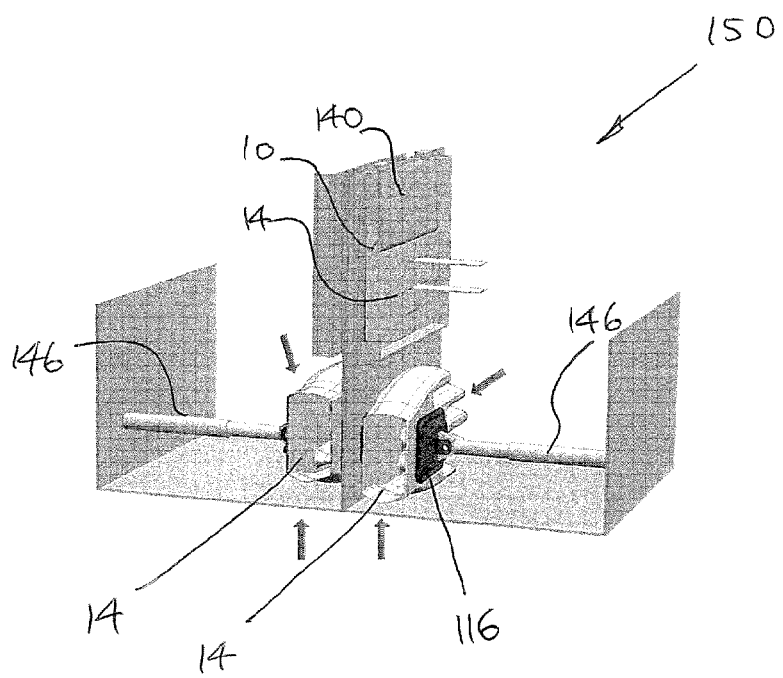
FIG. 26 shows a perspective, schematic view of a further embodiment of a glove dispensing machine in accordance with the present disclosure, with two disposable gloves shown in the open position.

In the embodiment shown, there is one cartridge of stacked, aligned disposable gloves shown. In use, a user inserts their hand into the gloves in a 'thumbs up' orientation, which is suitable for fitting of a glove 14 to both a left or a right hand of a user when inserted alternately into the machine. In a further embodiment, as shown in FIG. 26, there is shown a glove dispensing machine 150 which has all of the functionality of the machine 136 shown in FIG. 24, and the same operating principles as shown in FIGS. 25(a) to 25(f), but which has a mirror image machine arrangement of identical functionality (a back-to-back combination of two machines 136). Such a dual glove dispensing system allows two gloves 14 to be fitted to the left and right hands of a user simultaneously, as shown in FIG. 26, where the two gloves are each shown in the open configuration to enable admission of a human hand. In both portions of the apparatus, the gloves are stacked in the same direction in both cartridges or boxes, in a 'thumbs up' configuration.

Figures 27A, 27B:
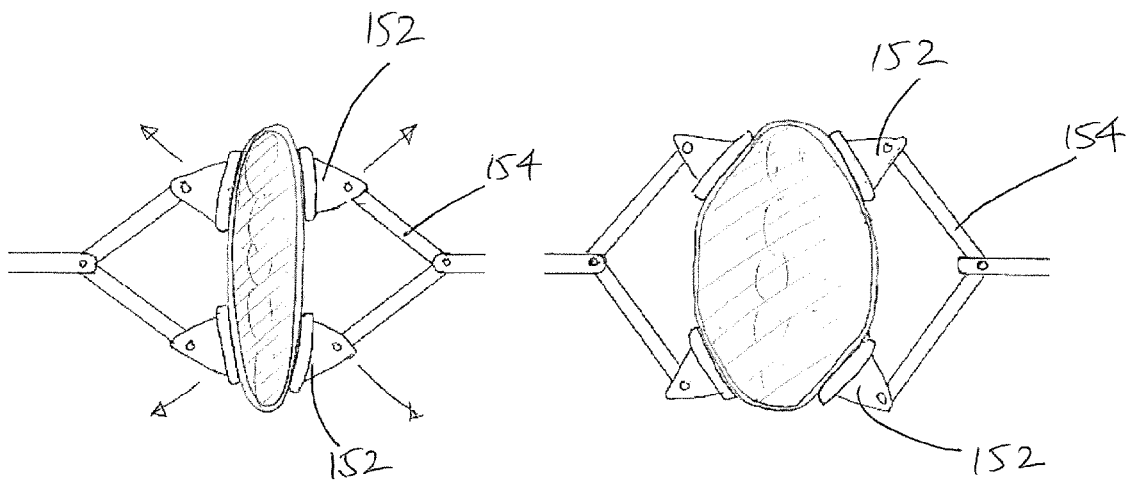
FIGS. 27(a) and 27(b) shows a side, schematic view of a further embodiment of a portion of the mechanism of a glove dispensing machine in accordance with the present disclosure, in FIG. 27(a) showing the mechanism attached to a disposable glove in a collapsed configuration, and in FIG.

In other embodiments of the machine shown in FIGS. 24 and 26, the arm holding the first suction cup may also have an articulated functionality rather than just being telescopic, for example. In some embodiments where a suction cup device is employed, one further arrangement can include the use of multiple, small articulated suction cups 152 fitted to the end of an articulated or telescopic arm 154, as illustrated in FIGS. 27(*a*) and 27(*b*). In this arrangement, pairs of small suction cups 152 are employed on each of the large faces 118, 120 of each glove 14, to be able to better stretch open the glove sufficiently wide at its open (cuff) end 22 to enable to admission of a human hand, by making the glove entry end more rounded in shape.

Referring now to the embodiment shown in FIG. 30, and in FIGS. 31(*a*) to 31(*d*), a dispensing machine 170 is shown in which a horizontal stack of gloves 14 is located in an open box 56 including a cartridge 10. The gloves 14 can be dispensed, one at a time, by the machine 170 which offers the glove to the user's hand in a vertical (or 'thumbs up') orientation without movement of the cartridge 10 from its initial position within the machine 170. The machine shown 170 (FIG. 31(*a*)) has a single, centrally-located, articulated arm 172 which operates using a telescopic extension and retraction mechanism and is arranged in use to move in a vertical direction upward or downward along the axis (X-X) of its length. The lowermost end region of the articulated arm 172 is fitted with is fitted with a suction device in the form of a first suction cup 116, of the type previously described in relation to FIG. 20 and FIG. 21. The articulated arm 172 is arranged in use to move the first suction cup 116 into a position to contact the glove 14, and then the suction cup 116 is actuated (that is, a suction pressure is applied) to retain one face (in this case the dorsal side 120, not the palmar side 118) of a single glove 14 by the application of the suction, as shown in FIG. 31(*b*). Actuation of the first suction cup 116 to retain the glove 14 then allows the retained glove to be moved by the action of the articulated arm 172 as the arm 172 is raised upward within the dispensing machine 170 directly above the cartridge 10. The glove 14 is lifted out from the cartridge or box 56 of horizontally stacked gloves, and is raised into a position above the cartridge 10, as shown in FIG. 31(*b*).

The suction cup 116 is joined to the articulated arm 172 at a terminal end region or head region 174 of the articulated arm. The head region 174 comprises a mounting bracket 176 as a support for the suction cup 116, and the bracket 176 itself is joined to the articulated arm 172, and is also pivotable thereabout, via a ball and socket joint 178.

Such a connection has a number of different degrees of freedom to allow greater flexibility for orienting the position of the suction cup 116 in relation to the glove(s) 14 when they are initially located in the cartridge or box 56. If the gloves 14 are not supplied evenly stacked and aligned in the cartridge 10 when supplied (for example if there are no finger or cuff or side alignment projections located within the cartridge), then there may be variations of up to 15-20 degrees in the angle of the uppermost glove from perfect horizontal alignment. For this reason, the ball and socket joint 178 creates a flexibly moveable paddle mounting for the suction cup 116, which is fully pivotally rotatable about the axis (X-X) of the articulated arm (that is, through 360 degree angle shown by Arrow B in FIG. 31(*b*) and also in FIG. 32), and it can also be angularly rotatable (up to a 90 degree angle as shown by Arrow A in FIG. 31(*c*) and also in FIG. 32) so that the central axis (Y-Y) of the head region 174 and mounting bracket 176 is moved out of coaxial alignment with the axis (X-X) of the elongate articulated arm 172. A glove contact and removal mechanism which features a ball and socket joint 178 offers freedom of movement in both a swing plane as well as in a pitch plane, which allows the contact and retention of even misaligned stacked gloves 14 when these are encountered in the cartridge 10 or box 56 by the suction cup 116.

Referring now to FIG. 31(*c*), next step in the sequence of operation of this dispensing machine 170 is that the head region 174 is then controlled to rotate (through angle shown by Arrow A) into an orientation in which the central axis (Y-Y) of the head region 174 and mounting bracket 176 is orthogonal to the axis (X-X) of the elongate articulated arm 172, but more importantly has now been brought into coaxial alignment with the axis of orientation (Z-Z) of the glove anchoring means. The glove 14 being carried by the activated suction cup 16 is thus now oriented orthogonally with respect to its original horizontal position, and is in a vertical (or "thumbs up") orientation, as shown in FIG. 31(*c*). Once the glove 14 is in this vertical orientation, the entire articulated arm 172 and head region 174 is then arranged to be moved (by a mechanism not shown within the bracketed track 180) in a direction away from its position above the cartridge or box 56 and (as shown by Arrow M) towards the anchoring means in the form of a second suction cup 122, which is supported in a mounted position at an interior wall of the machine 170. Once the suction cup 122 makes contact with the other side of the glove 14 (the other one of the palmar side 118 or the dorsal side 120 which is not already attached to the first suction cup 116), then the second suction cup 122 can then be actuated so as to retain the said other side of the glove by the application of suction (this position is shown in FIG. 31(*d*)). This means that the glove 14 is now held on both of its greater side faces 118, 120 by a respective suction cup 116, 122, and is therefore able to be stretched open if the entire articulated arm 172, head region 174 and suction cup 116 is arranged to be laterally driven a short distance back along the bracketed track 180 in a reverse direction (the opposite of Arrow M) so that the second suction cup 122 is moved in a direction away from the respective other suction cup 116. In the embodiment of this position shown in FIG. 30, the glove 14 is stretched sufficiently wide at its open end 22 to enable admission of a human hand. The user can thus insert their hand into the open (cuff) end 22 of the glove 14 without the need to touch the exterior of the glove, and whilst the glove is presented in a 'thumbs up' orientation. Once the hand is inserted in the glove, the suction pressure being applied to both suction cups 116, 122 can be deactivated, allowing the release of the sides 118, 120 of the gloves from the suction cups 116, 122, so that a user can retract a gloved hand from the apparatus. A view of the final position after the glove 14 has been dispensed is shown in FIG. 31(*e*).

Referring now to FIGS. 34 and 35, a further feature to improve the operation of the head region 174 of the articulated arm 172 can be the use of an optical sensor 182 which is mounted at the side of the mounting bracket 176 in use as a means for detecting the position of gloves 14 which are not evenly stacked and aligned in the cartridge 10 when supplied. In one form, the optical sensor 182 can be a laser scanner, the output signals from which can be used to adjust the rotational and angle pivoting of the head region 174 (that is, through a 360 degree angle shown by Arrow B and up to a 90 degree angle as shown by Arrow A) so that the suction cup 116 located at the mounting bracket 176 is able to be oriented to more evenly face onto the outer surface of the glove, or to be aligned with a physical feature of the gloves 14 (for example, an edge cuff) and therefore to improve contact and retention of even misaligned stacked gloves 14 at the suction cup 116.

In all of the preceding embodiments, the representative shape of the devices which contact and retain the glove at the articulated arm by means of air suction pressure are all representatively shown as being a suction cup 116, which has a square shaped front face. However, these suction devices may be embodied in many other forms appropriate to the retention of an object such as a disposable hand glove. For example, in FIG. 36, the suction pad 184 is shown mounted at right angles to the articulated arm 172, and has an inverted T-shaped front face, which can support a glove when oriented sideways and 'thumbs-up' where, in use, the thumb part of the glove is retained at the uppermost narrow portion 186 of the pad 184, and the (dorsal) main side of the glove 14 is held at the main rectangular region 188 of the pad 184. In this example, the surface of the pad 184 is smooth and has small air suction holes 185 located around the perimeter. In FIG. 37, an alternative version of a suction device 190 is shown, which has the same overall T-shaped pad 190 as the one shown in FIG. 36, but the suction holes 192 are larger and spaced evenly in rows over the whole pad 190 surface. In a still further representative embodiment in FIG. 38, the surface area of the face of the pad 194 is smooth with small air suction holes 196 thereacross, and the pad is in the shape of a whole glove hand, including suction holes to support the fingers of the gloves.

In circumstances where gloves are made available to the surface of such suction devices, all of the holes are covered by a face or finger of the glove, otherwise loss of vacuum will occur. It is envisaged that an air suction mechanism which isolates any suction pad hole not aligned with or covered by a part of the glove is necessary, otherwise there may be a loss of vacuum through an unengaged hole.

In any of the embodiments described, the motion of the telescopic arms may employ pneumatic pistons coupled to each arm and which respectively extend and retract to move the arms toward and away from each other. In any of the embodiments described, instead of using a suction cup it would also be possible to employ an adherent surface coating on the ends of the various moving arms or anchor points within the machine. As will be understood, the adherent substance is sufficiently tacky for each of the gloves to adhere to the corresponding arm or anchor point so that the glove sides are drawn apart whereby the cuff of the glove is opened as the arms are subsequently moved apart from one another by an arm drive assembly.

As the adhesiveness of the afore-mentioned adherent substance coated on the arms may gradually diminish after repeated glove opening operations due to the adherent substance being worn off or as a result of detritus sticking to the surfaces, the arms can be removed and replaced by new arms having a fresh coating of adherent substance, or new panels or pieces fitted to the ends of the various arms with fresh adherent substance. Alternatively, each of the arms may be periodically removed from the glove dispensing apparatus and washed or otherwise cleaned to remove any unwanted foreign detritus that has accumulated on the adherent surface(s).

It is expected that the glove dispensing machine would be table-mounted or wall-mounted, which is more suitable for being on a bench in a laboratory, a food preparation area, or a surgical scrub area, surgery etc. The machine in two forms shown in FIGS. 28 and 29 is a box-like device 160, which has a hand entry point 162 at the normal range of standing human hand height, as illustrated. The machine has front windows of glass or plastic 164 to enable a user 166 to see inside during the glove opening process, as well as to know when to reload boxes or cartridges as required. There is also a keypad or a touchscreen 168 that would give information to the user (and the state of filling of the machine). In one form, there would be a proximity sensor before which a user could motion their hand, and cause a glove to be dispensed.

In any of the embodiments described, to further enhance hygiene, at least some glove dispensing machines 112, 126, 136 may further include one or more ultraviolet (UV) light sources provided within the box-like housing 160 for surface treatment of the gloves 14 with sterilizing UV light (for example, UV light in a wavelength range of from 200 nm to 280 nm and preferably, in the range of from 250 nm-280 nm). The UV light source(s) may, for instance, be selected from UV lamp(s) or UV light emitting diodes (for example, UV LED strips including multiple spaced apart UV emitting LEDs). In one example, a UV LED strip can be mounted in the interior of the machine housing 160, facing the cartridge 10 of undispensed gloves 14.

For safety reasons, the UV light source(s) is/are typically switched off during the step of opening of the open (cuff) end 22 of the glove 14 whilst the user's hand is located in the machine 112, 126, 136, and during insertion of the hand into the glove 14. This can be achieved for example when the proximity sensor or the touchscreen 168 is actuated. Desirably also, the UV light source(s) can only operate when a cover of the hand entry point 162 is closed. Further, in at least some embodiments, the duration of operation of the UV light source(s) is controlled by a control system, and may only be switched back on by the control system after a predetermined period of time following detection of the withdrawal of the user's hand from the hand entry point 162 by a proximity sensor as described above. However, any safe mode of operation of the UV light source(s) can be employed.

The gloves mentioned in this disclosure will be lightweight and may include the sandwich gloves of the type commonly used in sandwich bars, delicatessens and like food outlets involving the handling and preparation of food for a customer, however any suitable glove type whereby the layers of the glove can adhere to, and be drawn apart, for donning of the glove as described herein may be utilised. The gloves may, for example, be polyethylene (PE), vinyl (polyvinyl chloride), nitrile (carboxylated butadiene-acrylonitrile) or polyester gloves. Typically, the gloves with be selected from lightweight, polyethylene (PE) gloves.

The apparatus described for dispensing gloves may also include a recognition system configured to recognise whether the cartridge of gloves is a genuine, authorised product (i.e., an OEM cartridge) for use in the dispensing apparatus, or a non-genuine aftermarket item. In one embodiment, the apparatus may only become operational after recognising the cartridge as being genuine. According to such a configuration, in one for more forms, the control system may implement a processor which is communicable with an interrogation system operable to interrogate an information encoding device located on the product. Herein the term "processor" is used to refer generically to any device that can process instructions based on programmed code and may include: a microprocessor, microcontroller, programmable logic device or other computational device, a general-purpose computer (e.g., a PC) or a server.

In one embodiment, the interrogation system can comprise an RFID reader that is controlled to read an information encoding device in the form of an RFID tag (e.g., an RFID smart label) located on the cartridge (e.g., affixed by a suitable adhesive). The RFID tag may be encoded with any desired information that can be read by the RFID reader and subsequently interpreted by the processor as being representative of a genuine glove cartridge. In an alternative embodiment, the information encoding device may comprise a QR code or barcode disposed on the cartridge and readable by an image scanner implemented by the processor. For example, the QR code or barcode may be printed on respective of the gloves, or a label bearing the QR code or barcode may be affixed to a leading one of the gloves in a position to be read by the image scanner as the line of gloves is fed into position for dispensing of the gloves in use. However, any suitable arrangement or location of the information encoding device on the cartridge of gloves is expressly encompassed. It will also be understood that the recognition system and information encoding device should not be seen as being limited to those forms described above and may comprise any suitable electronic or electro-mechanical interrogation arrangement.

Additionally, the control system may further include suitable communications hardware and software for communicating with a remote system (e.g., via the Internet) for determining whether the information extracted from the information encoding device is associated with a genuine cartridge of gloves. The remote system may, for example, implement a server computer system for receiving and sending communications to the control system.

Further, the control system may be operable, under the control of the processor, to communicate with the remote system for glove ordering purposes. For example, the processor may be communicable with a sensor that detects and outputs a signal when a new cartridge of gloves has been inserted into the dispenser. Responsive to detecting the sensor signal, the processor may cause the control system to send a communication to the remote system to indicate that a new cartridge of gloves has been inserted into the dispenser. Responsive to receiving the communication, the remote system generates an order for dispatching one or more new cartridges of the gloves to an address registered for the corresponding glove dispensing apparatus (e.g., identified by an address or other suitable identification information sent with the communication). In at least some embodiments, for instance, the remote system may count, or otherwise effect the recording of, the number of glove cartridges inserted into the dispenser over a period of time (e.g., days or weeks), and place an order for dispatch of one or more new glove cartridges (e.g., one or more boxes of new glove cartridges) for timely delivery to the registered address to ensure the registered user of the dispenser does not run out of the disposable gloves, and has sufficient cartridges(s) of the gloves available to meet their needs.

From the above, it will be understood that at least some embodiments of gloves and/or dispensing apparatus in accordance with the invention provide one or more of the following advantages.

The gloves can be rapidly and conveniently presented in an opened condition for donning by the user.

The provision of the gloves in a cartridge as described herein avoids multiple gloves being drawn from a box at the same time as in the prior art.

The gloves can be opened and donned without the user touching the exterior of the gloves with their bare hands, thereby reducing the risk of contamination of the gloves and enhancing hygiene.

The cartridge of gloves can be quickly loaded into the glove opening apparatus.

The glove opening system provides an elegant solution for opening of the gloves with a relatively low number of moveable parts.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

The reference in this specification to any prior publication or information is not, and should not be taken as, an acknowledgement or admission or any form of suggestion that the prior publication or information forms part of the common general knowledge in the field of endeavor to which this specification relates.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In addition, the foregoing describes only some embodiments of the invention(s), and alterations, modifications, additions and/or changes can be made thereto without departing from the scope and spirit of the disclosed embodiments, the embodiments being illustrative and not restrictive.

Furthermore, invention(s) have described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention(s). Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

The invention claimed is:

1. A machine arranged for dispensing a disposable glove, the machine comprising:
   an articulated arm arranged in use for contacting and retaining a first part of the glove and for moving said glove from a first position in which the glove is located in a cartridge containing one or more gloves, to a second position in which a second part of the said glove is able to be contacted with and retained by an anchoring means,
   wherein, once in the second position, one or both of the articulated arm or anchoring means is moveable in a direction relative the other, in use so as to stretch the glove sufficiently wide at an open end thereof to enable admission of a human hand.

2. A The machine as claimed in claim 1, wherein the articulated arm moves pivotally as it moves the glove to the second position.

3. A The machine as claimed in claim 1, wherein the anchoring means is arranged at a support arm, which itself is moveable so as to move the anchoring means into the second position.

4. A The machine as claimed in claim 1, wherein the articulated arm is elongate, and is moveable in an axial direction along its length, both toward and away from the cartridge.

5. The machine as claimed in claim 4, wherein after the glove has been moved from the first position, the cartridge is laterally moveable out of alignment with the axial direction of movement of the articulated arm.

6. The machine as claimed in claim 5, wherein said lateral movement of the cartridge exposes the anchoring means, the anchoring means being located in alignment with the axial direction of movement of the articulated arm.

7. The machine as claimed in claim 6, wherein in use, further movement of the articulated arm along its said axial direction of movement and towards the anchoring means shall move said glove into the second position.

8. The machine as claimed in claim 7, wherein a head region of the articulated arm is joined to and pivotable about the axis of the articulated arm, to enable the head region to be aligned with the orientation of the glove when the glove is in the first position, as part of moving said glove away from the first position.

9. The machine as claimed in claim 8, wherein the head region of the articulated arm is fitted with an alignment sensing device to enable the head region to be aligned with a physical feature of the glove, to improve contact with and retention of the glove at the articulated arm.

10. The machine as claimed in claim 8, wherein the articulated arm is elongate, and is moveable in an axial direction along its length, one such movement being away from the cartridge, as part of moving the said glove away from the first position.

11. The machine as claimed in claim 1, wherein the contact and retention of the glove at the articulated arm, or if applicable at a head region of the articulated arm, is by means of a suction device, which uses air pressure to retain the respective first or second side of a glove thereto.

12. The machine as claimed in claim 11, wherein the contact and retention of the glove at the anchoring means is by means of a suction device, which uses air pressure to retain the other of the respective first or second side of a glove thereto.

13. A method for dispensing a disposable glove, the method comprising the steps of:
moving an articulated arm to contact and retain a first part of the glove which is located in a first position located in a cartridge;
moving said glove out of the cartridge toward a second position, in which a second part of the said glove is able to be contacted with and retained by an anchoring means; and
wherein, once in the second position, the step of moving one or both of the articulated arm or anchoring means in a direction relative the other, in use so as to stretch the glove sufficiently wide at an open end thereof to enable admission of a human hand.

14. The method as claimed in claim 13, wherein the step of contacting and retaining the glove when in the first position at the articulated arm is achieved by the step of activation of a suction device.

15. The method as claimed in claim 13, wherein the step of moving the glove toward the second position is achieved by activation of the movement of the articulated arm to cause it to pivot, or to cause it to move in a direction along its axial length.

16. The method as claimed in claim 13, wherein the step of moving an articulated arm to contact and retain a first part of the glove further includes pivoting a head region of the articulated arm about the axis of the articulated arm so as to align the head region with the glove, this step guided by an alignment sensing device to detect a physical feature of the glove.

17. The method as claimed in claim 16, wherein moving the glove into the second position where a second part of the said glove is able to be contacted with and retained by an anchoring means includes the step of rotation of an axis of the head region of the articulated arm which is carrying said glove into alignment with an axis of orientation of the anchoring means.

18. The method as claimed in claim 17, wherein moving the glove into the second position where a second part of the said glove is in contact with and retained by the anchoring means comprises the step of moving the articulated arm and head region in a direction towards the anchoring means.

19. The method as claimed in claim 13, wherein the contact and retention of the glove in the second position at the anchoring means is achieved by the step of activation of a suction device.

\* \* \* \* \*